US012098353B2

(12) United States Patent
McCain et al.

(10) Patent No.: US 12,098,353 B2
(45) Date of Patent: Sep. 24, 2024

(54) FLUIDIC DEVICE FOR LONG-TERM EXPLANT CULTURE AND IMAGING

(71) Applicant: University of Southern California, Los Angeles, CA (US)

(72) Inventors: Megan McCain, Los Angeles, CA (US); Joycelyn Yip, Los Angeles, CA (US); Ching-Ling Lien, Los Angeles, CA (US); Michael Harrison, Los Angeles, CA (US)

(73) Assignees: University of Southern California, Los Angeles, CA (US); Children's Hospital of Los Angeles, Los Angeles, CA (US)

( * ) Notice: Subject to any disclaimer, the term of this patent is extended or adjusted under 35 U.S.C. 154(b) by 0 days.

(21) Appl. No.: 18/124,923

(22) Filed: Mar. 22, 2023

(65) Prior Publication Data

US 2023/0250379 A1 Aug. 10, 2023

Related U.S. Application Data

(62) Division of application No. 16/654,489, filed on Oct. 16, 2019, now Pat. No. 11,629,320.

(Continued)

(51) Int. Cl.
*C12M 3/06* (2006.01)
*A01N 1/02* (2006.01)
(Continued)

(52) U.S. Cl.
CPC ........... *C12M 23/16* (2013.01); *A01N 1/0247* (2013.01); *B01L 3/502715* (2013.01);
(Continued)

(58) Field of Classification Search
CPC ...... C12M 23/16; C12M 23/22; C12M 23/24; A01N 1/0247; B01L 3/502715;
(Continued)

(56) References Cited

U.S. PATENT DOCUMENTS 11,629,320 B2 * 4/2023 McCain ................. C12M 23/16
435/1.2
2015/0360224 A1 12/2015 Zhang et al.
(Continued)

*Primary Examiner* — Brian J. Sines
(74) *Attorney, Agent, or Firm* — Brooks Kushman P.C.

(57) ABSTRACT

Zebrafish are a powerful model for investigating cardiac repair due to their unique regenerative abilities, scalability, and compatibility with many genetic tools. However, characterizing the regeneration process in live adult zebrafish hearts has proved challenging because adult fish are opaque and explanted hearts in conventional culture conditions experience rapid declines in morphology and physiology. To overcome these limitations, we fabricated a fluidic device for culturing explanted adult zebrafish hearts with constant media perfusion that is also compatible with live imaging. Unlike hearts cultured in dishes for one week, the morphology and calcium activity of hearts cultured in the device for one week were largely similar to freshly explanted hearts. We also cultured injured hearts in the device and used live imaging techniques to continuously record the revascularization process over several days, demonstrating how our device enables unprecedented visual access to the multi-day process of adult zebrafish heart regeneration.

4 Claims, 14 Drawing Sheets

(8 of 14 Drawing Sheet(s) Filed in Color)

Related U.S. Application Data

(60) Provisional application No. 62/746,666, filed on Oct. 17, 2018.

(51) Int. Cl.
*B01L 3/00* (2006.01)
*C12M 1/00* (2006.01)
*C12M 1/04* (2006.01)

(52) U.S. Cl.
CPC ............ *C12M 23/22* (2013.01); *C12M 23/24* (2013.01); *B01L 2200/0684* (2013.01); *B01L 2300/087* (2013.01); *B01L 2300/0877* (2013.01); *B01L 2300/12* (2013.01)

(58) Field of Classification Search
CPC ....... B01L 2200/0684; B01L 2300/087; B01L 2300/0877; B01L 2300/12
See application file for complete search history.

(56) References Cited

U.S. PATENT DOCUMENTS

2015/0362411 A1 12/2015 Zhang et al.
2019/0359924 A1 11/2019 Kerns et al.

\* cited by examiner

FLUIDIC DEVICE FOR LONG-TERM EXPLANT CULTURE AND IMAGING

CROSS-REFERENCE TO RELATED APPLICATIONS

This application is a division of U.S. patent application Ser. No. 16/654,489 filed Oct. 16, 2019, now U.S. Pat. No. 11,629,320 B2 issued Apr. 18, 2023, which claims the benefit of U.S. provisional application Ser. No. 62/746,666 filed Oct. 17, 2018, the disclosures of which are hereby incorporated in their entirety by reference herein.

STATEMENT REGARDING FEDERALLY SPONSORED RESEARCH OR DEVELOPMENT

This invention was made with government support under R01HL130172 awarded by National Institutes of Health/National Heart, Lung, and Blood Institute. The government has certain rights in the invention.

TECHNICAL FIELD

In at least one aspect, the present invention is related to fluidic devices for culturing and imaging organs.

BACKGROUND

Adult human myocardium has an extremely limited regenerative capacity (1). As a result, major cardiac injuries, such as myocardial infarctions, are irreversible and often lead to severe long-term complications, including heart failure (2). Unlike humans, the adult myocardium of several non-mammalian vertebrates can regenerate, including that of the zebrafish (3-7). The adult zebrafish heart can fully regenerate within two months after up to 20% of the ventricle is resected (8) largely due to the ability of pre-existing cardiac myocytes to undergo limited dedifferentiation followed by proliferation (9, 10). Many non-myocyte components of the myocardium, such as epicardial cells (11), the vasculature (12, 13), and the extracellular matrix (14), also play important roles in regeneration. However, how the collective cellular and acellular features of the heart interact and cooperate to accomplish regeneration is incompletely understood. Establishing these details is the first step towards potentially translating mechanisms of zebrafish heart regeneration to human heart repair.

The existing gaps in knowledge related to adult zebrafish heart regeneration are in large part due to the limitations of existing experimental tools to interrogate this process. Although epicardial cells (15) and cardiac myocytes (16, 17) from adult zebrafish hearts have successfully been isolated and cultured in vitro, these monolayer cultures of a single cell type cannot be used to investigate cell-cell interactions or organ-level mechanisms of regeneration. These types of questions are usually addressed by injuring hearts in vivo and employing histological methods to evaluate features, such as wound size and cellular proliferation, at different time points after surgery as snapshots (11). However, this strategy provides limited dynamic information, such as pathways of cell migration or origins of different cell types.

Because adult zebrafish are not transparent, imaging explanted hearts ex vivo is the only option for imaging heart regeneration in real-time. Today, explanted hearts are usually cultured in Petri dishes or multi-well plates. In these static conditions, hearts experience rapid declines in native-like morphology and function within three days (18), introducing artifacts that render them largely unusable for monitoring regeneration, a multi-day process. These morphological and functional declines have been partially alleviated in a subset of hearts that undergo gentle agitation in culture dishes (19). However, because the hearts are not confined to a specific location or orientation, agitation culture is not compatible with continuous live imaging, which is required to monitor processes that occur over several hours, such as cell migration.

In recent years, microfabricated fluidic devices have been implemented to culture arrays of zebrafish embryos and larvae for up to 72 hours, often with constant media perfusion to maintain viability (20-22). Within these devices, each organism is cultured within a compartment slightly larger than the organism itself, which facilitates continuous live imaging over several hours or days by minimizing arbitrary motion and preserving the orientation of the organism.

SUMMARY

In at least one aspect, the present invention provides an innovative fluidic chip system that holds juvenile or adult zebrafish hearts in a single position, provides a continuous media flow, fits into conventional optical and fluorescent imaging systems, and allows for post-analysis specimen recovery. Unlike existing fluidic culture devices, it focuses on supporting a specific organ for at least one week while preserving organ structure and function in comparison to standard cell culture techniques. Produced using rapid prototyping and soft lithography techniques, these devices are suitable for medium to high scale production and are easily customizable to other explanted organs or organoids that are 1-10 mm in diameter. The effectiveness of this device for long-term explant culture is demonstrated by comparing the functional and histological characteristics of zebrafish hearts in traditional culture conditions and hearts in the chips with perfusion. The effectiveness of this device for live imaging is demonstrated by imaging the revascularization of an injured zebrafish heart maintained in the device for 4.5 days.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

For a further understanding of the nature, objects, and advantages of the present disclosure, reference should be had to the following detailed description, read in conjunction with the following drawings, wherein like reference numerals denote like elements and wherein.

DETAILED DESCRIPTION

Figure 1A:
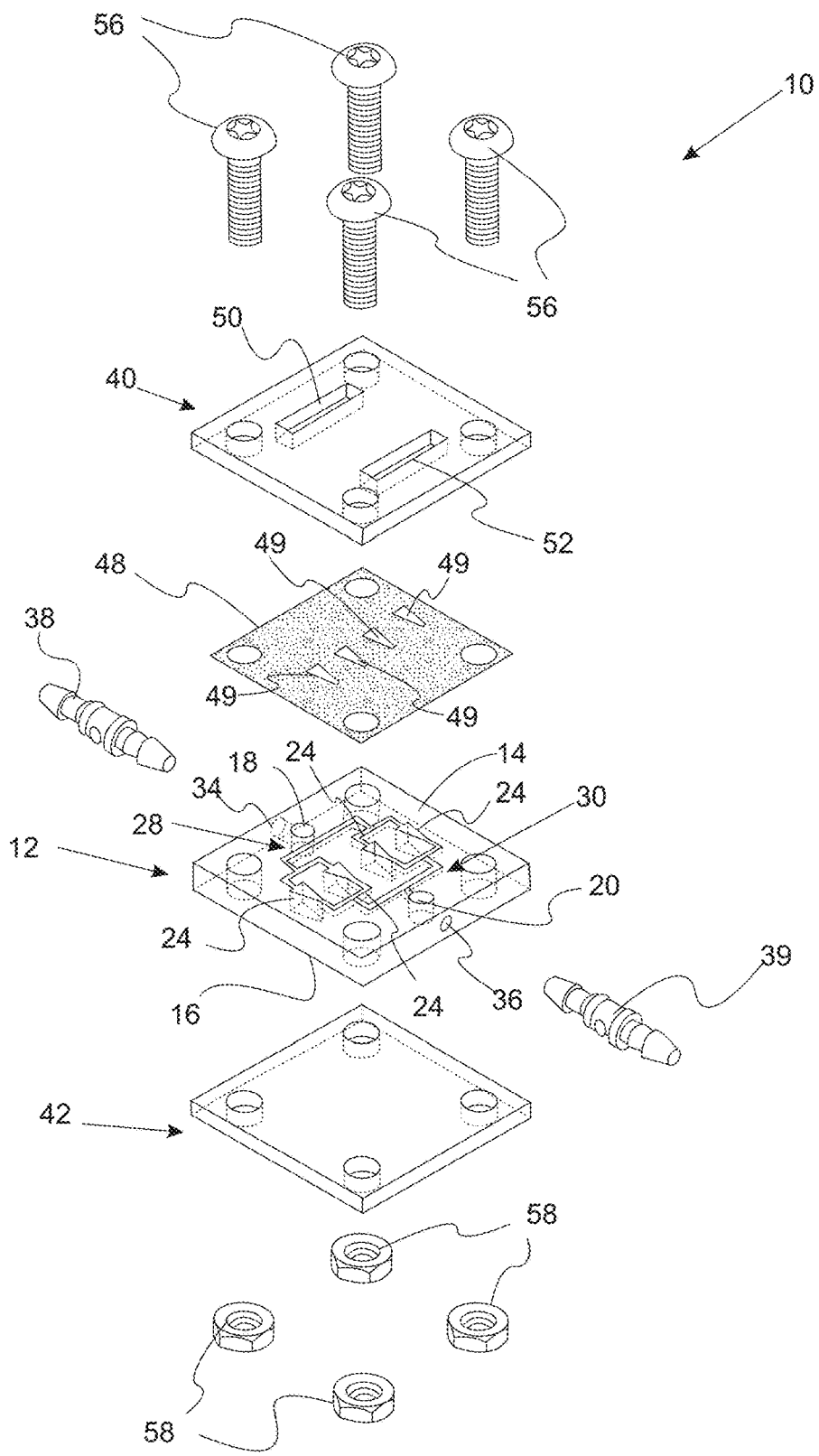
FIGS. 1A, 1B, and 1C. Design of the zebrafish heart device. (A) An exploded view of the entire device, including the center PDMS insert with the triangular wells and channels, the PTFE membrane, the transparent acrylic panels, the nuts and bolts, and the barbed connectors. (B) A perspective view of the assembled device. (C) A top view of the perspective device.
Figure 1B:
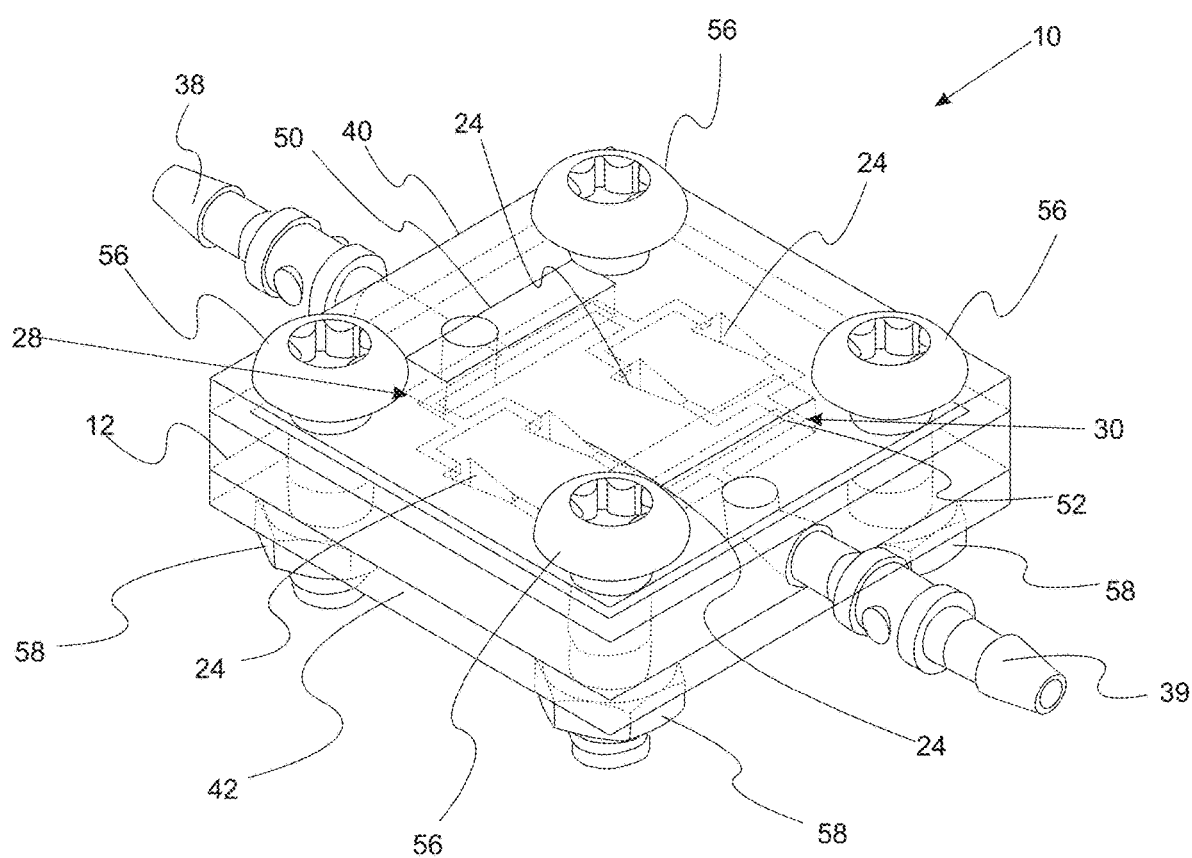
Figure 1C:
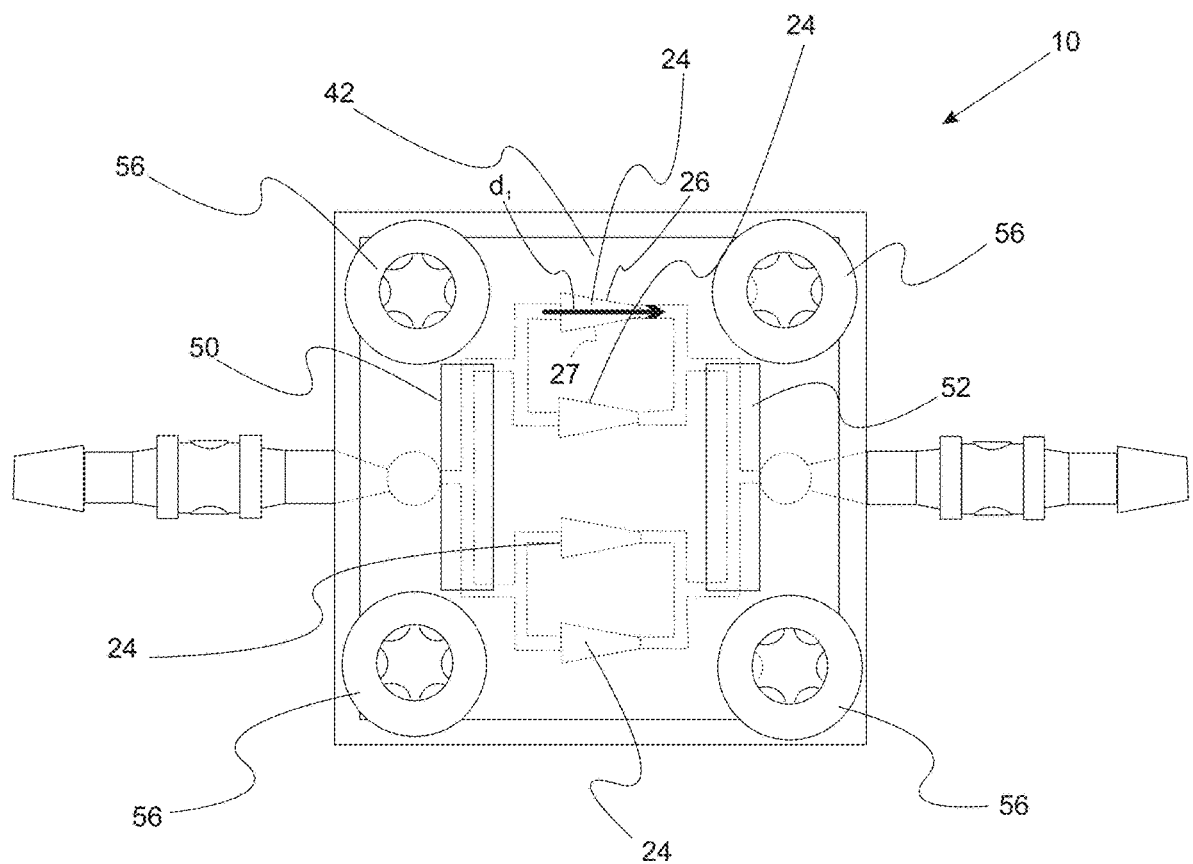

Reference will now be made in detail to presently preferred embodiments and methods of the present invention, which constitute the best modes of practicing the invention presently known to the inventors. The Figures are not necessarily to scale. However, it is to be understood that the disclosed embodiments are merely exemplary of the invention that may be embodied in various and alternative forms. Therefore, specific details disclosed herein are not to be interpreted as limiting, but merely as a representative basis for any aspect of the invention and/or as a representative basis for teaching one skilled in the art to variously employ the present invention.

It is also to be understood that this invention is not limited to the specific embodiments and methods described below, as specific components and/or conditions may, of course, vary. Furthermore, the terminology used herein is used only for the purpose of describing particular embodiments of the present invention and is not intended to be limiting in any way.

It must also be noted that, as used in the specification and the appended claims, the singular form "a," "an," and "the" comprise plural referents unless the context clearly indicates otherwise. For example, reference to a component in the singular is intended to comprise a plurality of components.

The term "comprising" is synonymous with "including," "having," "containing," or "characterized by." These terms are inclusive and open-ended and do not exclude additional, unrecited elements or method steps.

The phrase "consisting of" excludes any element, step, or ingredient not specified in the claim. When this phrase appears in a clause of the body of a claim, rather than immediately following the preamble, it limits only the element set forth in that clause; other elements are not excluded from the claim as a whole.

The phrase "consisting essentially of" limits the scope of a claim to the specified materials or steps, plus those that do not materially affect the basic and novel characteristic(s) of the claimed subject matter.

With respect to the terms "comprising," "consisting of," and "consisting essentially of," where one of these three terms is used herein, the presently disclosed and claimed subject matter can include the use of either of the other two terms.

It should also be appreciated that integer ranges explicitly include all intervening integers. For example, the integer range 1-10 explicitly includes 1, 2, 3, 4, 5, 6, 7, 8, 9, and 10. Similarly, the range 1 to 100 includes 1, 2, 3, 4 . . . 97, 98, 99, 100. Similarly, when any range is called for, intervening numbers that are increments of the difference between the upper limit and the lower limit divided by 10 can be taken as alternative upper or lower limits. For example, if the range is 1.1. to 2.1 the following numbers 1.2, 1.3, 1.4, 1.5, 1.6, 1.7, 1.8, 1.9, and 2.0 can be selected as lower or upper limits.

In the examples set forth herein, concentrations, temperature, and reaction conditions (e.g., pressure, pH, flow rates, etc.) can be practiced with plus or minus 50 percent of the values indicated rounded to or truncated to two significant figures of the value provided in the examples. In a refinement, concentrations, temperature, and reaction conditions (e.g., pressure, pH, flow rates, etc.) can be practiced with plus or minus 30 percent of the values indicated rounded to or truncated to two significant figures of the value provided in the examples. In another refinement, concentrations, temperature, and reaction conditions (e.g., pressure, pH, flow rates, etc.) can be practiced with plus or minus 10 percent of the values indicated rounded to or truncated to two significant figures of the value provided in the examples.

For any device described herein, linear dimensions and angles can be constructed with plus or minus 50 percent of the values indicated rounded to or truncated to two significant figures of the value provided in the examples. In a refinement, linear dimensions and angles can be constructed with plus or minus 30 percent of the values indicated rounded to or truncated to two significant figures of the value provided in the examples. In another refinement, linear dimensions and angles can be constructed with plus or minus 10 percent of the values indicated rounded to or truncated to two significant figures of the value provided in the examples.

Throughout this application, where publications are referenced, the disclosures of these publications in their entireties are hereby incorporated by reference into this application to more fully describe the state of the art to which this invention pertains.

Abbreviations:

"PDMS" means polydimethylsiloxane.

"PTFE" means polytetrafluoroethylene.

With reference to FIGS. 1A, 1B, 1C, 2A, 2B, 2C, and 3, schematic illustrations of a microfluidic device for imaging whole organs is provided. The microfluidic device is typically transparent at positions that allow imaging of organs, organoids, or organisms placed therein. Moreover, microfluidic assembly allows cultured medium to nourish explanted organs placed therein. Microfluidic assembly 10 includes polymeric block 12 having a top surface 14 and a bottom surface 16. Typically, polymeric block 12 is made from polymeric organosilicons such as PDMS. Polymeric block 12 defines an input reservoir 18 and an output reservoir 20. Typically, input reservoir 18 and output reservoir 20 extend from top surface 14 to approximately 0.5 mm from the bottom surface 16. Polymer block 12 also defines at least one triangular well 24 which extends from top surface 14 to bottom surface 16. Typically, polymeric bock 12 has a thickness from 1 mm to 10 mm. Triangular well 24 traps and maintains the orientation of explanted organs (e.g., zebrafish hearts), organoids, or organisms. The well is triangular in the sense of including sidewalls 26 and 27 which are angled with respect to each other such that these sidewalls approach each other along direction $d_1$. Direction $d_1$ is generally in the average direction of the liquid flow. The convergence of sidewalls 26 and 27 allow a specimen to be wedged in place thereby fixed its position and orientation. Advantageously, the microfluidic assembly can be used to culture mouse embryos/organs and human fetal organs. In a refinement, polymer block 12 defines a plurality of triangular wells 24 (e.g., 2 to 10) which allow multiple organoids, or organisms. to be studied in parallel.

Still referring to FIGS. 1A, 1B, 1C, 2A, 2B, 2C, and 3, polymer block 12 also defines first flow channel system 28 and second flow channel system 30. First flow channel system 28 is in fluid communication with the input reservoir 18 and the at least one triangular well. Similarly, second flow channel system 30 is in fluid communication with the output reservoir 20 and the at least one triangular well. Each of first flow channel system 28 and second flow channel system 30 include tracks that have a closed bottom and open top. Typically, each track in first flow channel system 28 and second flow channel system 30 have a depth from about 300 to 800 µm and a width from about 300 to 800 µm. The tracks of first flow channel system 28 and second flow channel system 30 enter and exit respectively triangular wells 24 at top surface 14. Moreover, the flow of media is uniformly distributed across first flow channel system 28 and second flow channel system 30, which are designed to be equal in hydraulic resistance as the media is perfused microfluidic assembly 10. Finally, polymer block 12 defines inlet conduit 34 in fluid communication with the input reservoir 18 and outlet conduit 36 in fluid communication with the output reservoir 20. Flow adapters/connectors 38, 39 can be placed in inlet conduit 34 and outlet conduit 36 to allow flow of a liquid media into and out of microfluidic assembly 10.

First transparent plate 40 is disposed over the top surface 14 of the polymeric block 12 and second transparent plate 42 disposed over the bottom surface 16 of the polymeric block. In a refinement, gas permeable membrane 48 is interposed between the first transparent plate 40 and the polymeric block 42. Gas permeable membrane 48 has several openings 49 that allow imaging of each of the triangular wells 24. In a refinement, gas permeable membrane 48 is a PTFE membrane. In a refinement, first transparent plate 40 defines a first vent slot 50 and a second vent slot 52 allowing gases to vent from the gas permeable membrane 48. First vent slot 50 overlays the input reservoir 18 and a portion of first flow channel system 28, and the second vent slot 52 overlays the output reservoir 20 and a portion of second flow channel system 30. Finally, polymeric block 12, first transparent plate 40, second transparent plate 42, and gas permeable membrane 48 are bolted together with bolts 56 and nuts 58 via suitable access holes in each of these components.

Figure 2A:
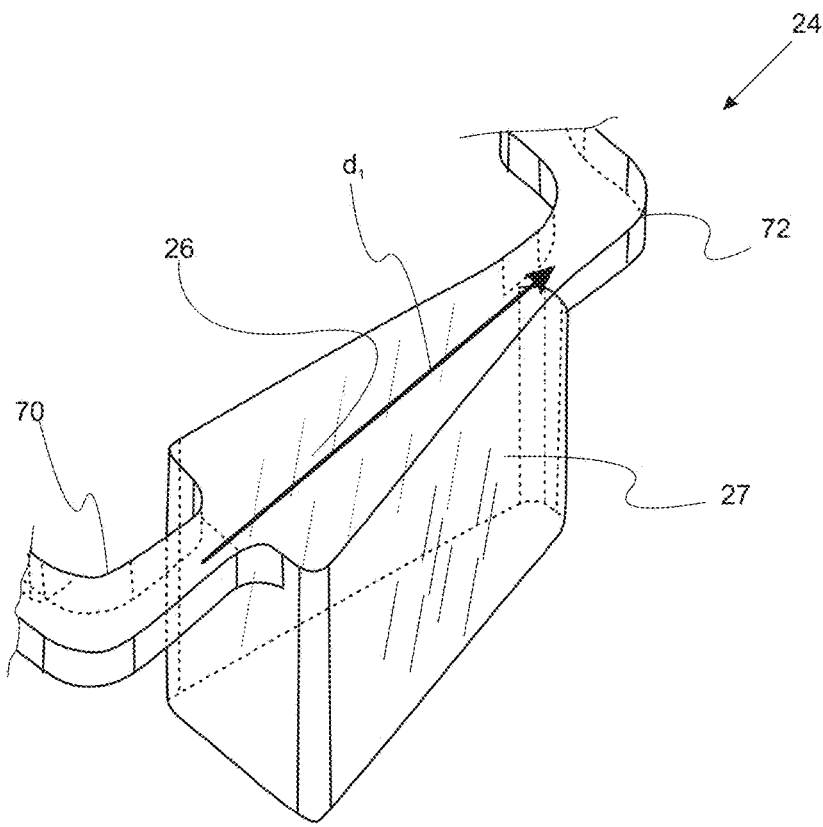
FIGS. 2A, 2B, and 2C. (A) Perspective view of a triangular well. (B) Side view of a triangular well. (C) Top view of a triangular well.
Figure 2B:
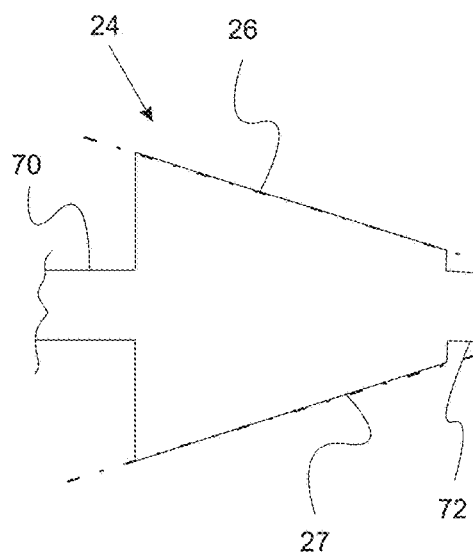
Figure 2C:
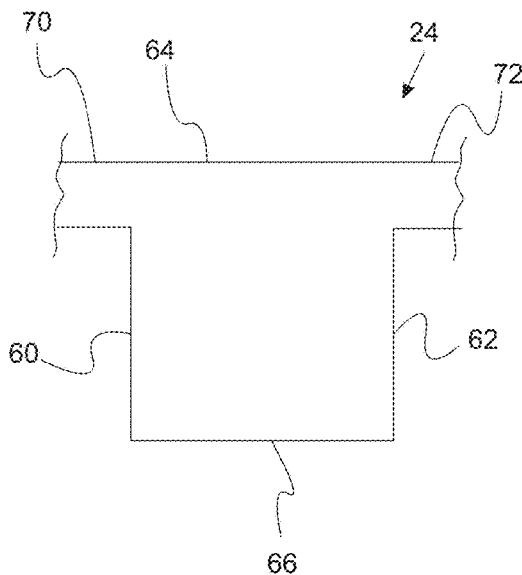

With reference to FIGS. 2A, 2B, and 2C, triangular well 24 is defined by converging sidewalls 26 and 27, upstream sidewall 60, and downstream sidewall 62, top wall 64, and bottom wall 66. Top wall 64 is defined by first transparent plate 40 while bottom wall 66 is defined by second transparent plate 42. Sidewalls 26 and 27 are generally planar and are angled with respect to each other such that these sidewalls approach each other along direction $d_1$. The imaginary extension of sidewalls 26 and 27 intersect at imaginary line $l_1$. The angle $a_1$ defined in a plane perpendicular to sidewalls 26 and 27 is an angle typically between 10 and 120 degrees. In a refinement, angle $a_1$ is from about between 30 and 90 degrees. Liquid flows into triangular well 24 via flow channel 70 which is part of first flow channel system 28. In a refinement, flow channel 70 enters triangular well 24 through an opening in upstream sidewall 60. Similarly, liquid flow out of triangular well 24 via flow channel 72 which is part of second flow channel system 30. In a refinement, flow channel 72 exists triangular well 24 through an opening in downstream sidewall 62. In a further refinement, each of flow channels 70 and 72 are positioned at the top of triangular well 24.

Figure 3:
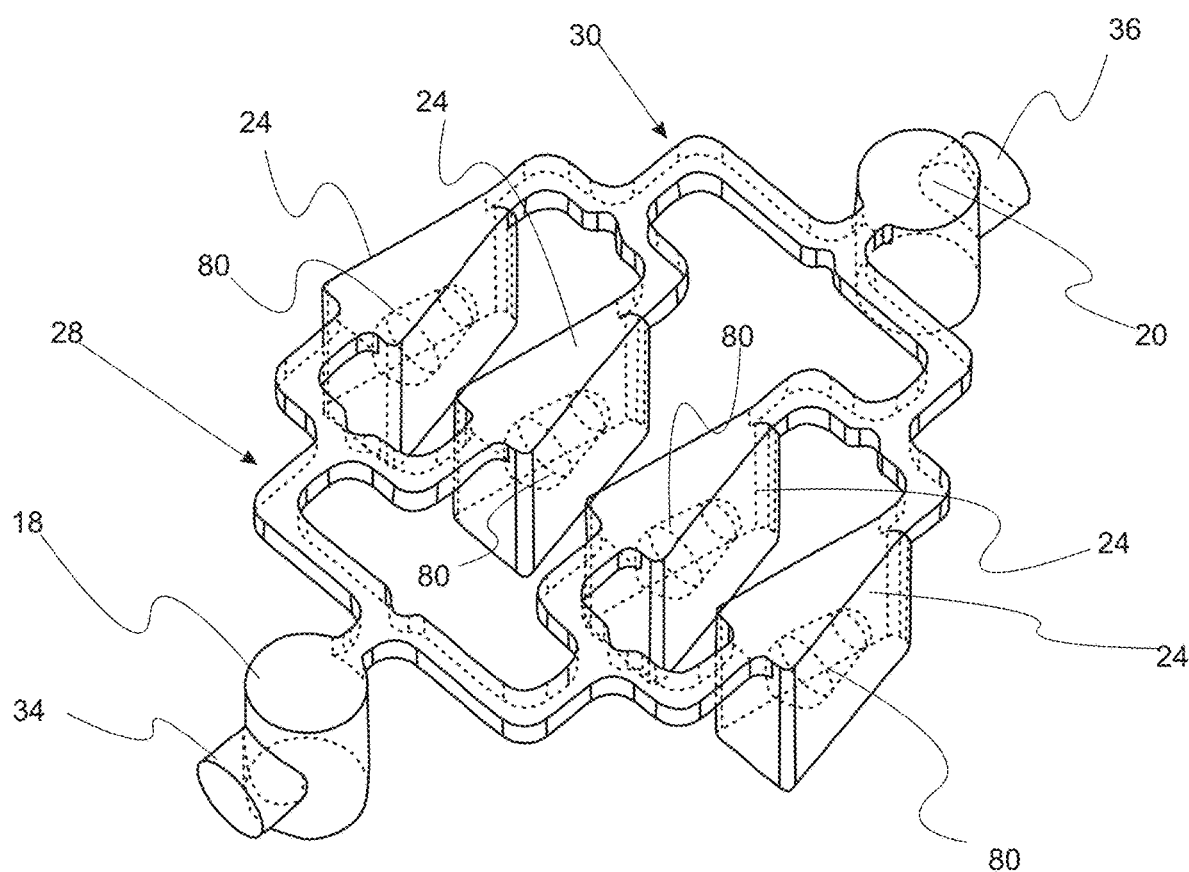
FIG. 3 provides a perspective view showing the complete flow system of the microfluidic assembly.

Referring to FIG. 3, a schematic of the flow channeling system defined by microfluidic assembly 10 is provided. Fluid is introduced into inlet conduit 34 and through each of triangular wells 24. An explanted organ 80 (e.g., zebrafish heart) is placed at the bottom of each of triangular wells 24. The triangular cross-section of the well maintains the orientation of the explanted organ during imaging.

In another embodiment, a method for imaging an explanted organ applying the microfluidic assembly set forth above is provided. The method includes a step of placing an explanted organ into the at least one triangular well and then continuingly flowing a culture medium into the microfluidic assembly. The explanted organ is imaged according to techniques known to those skilled in the art of organ culturing and imaging. As set forth above, microfluidic assembly 10 can include a plurality of triangular wells with an explanted organ (e.g., a zebrafish heart) being placed into each triangular well. Typically, the culture medium includes a fluorescent dye or indicator which enhances imaging of the organ.

Figure 4A:
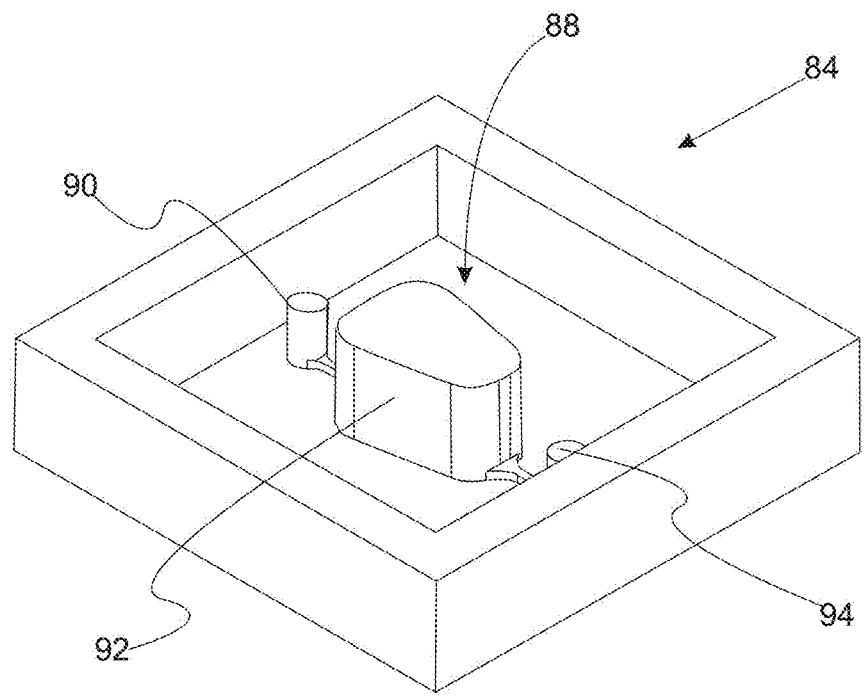
FIGS. 4A and 4B provide a perspective view of molds used to form the PDMS inserts of the microfluidic assemblies of FIG. 1.
Figure 4B:
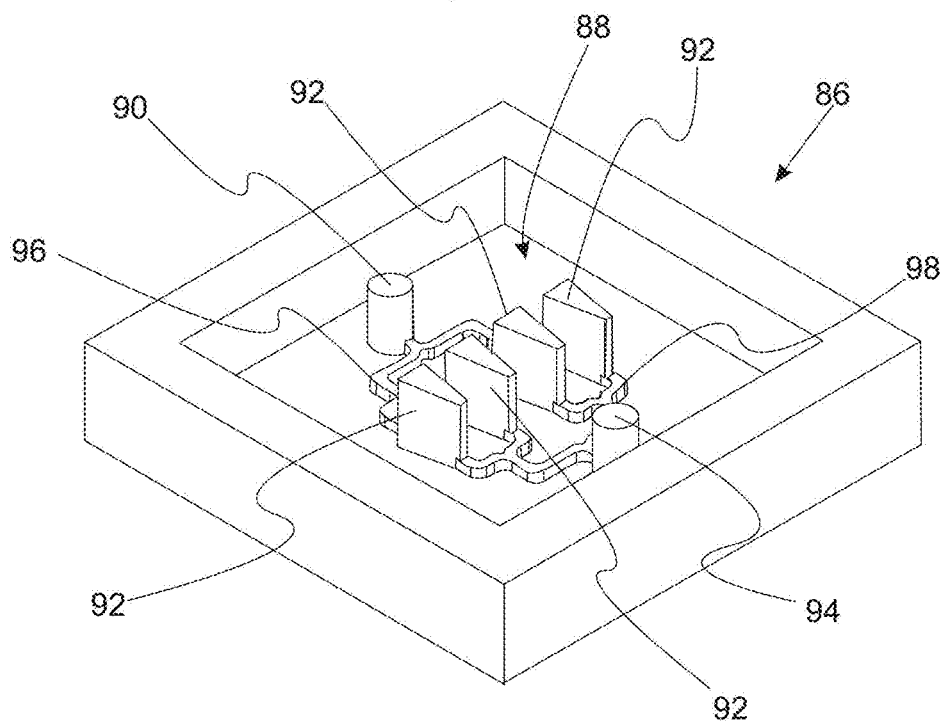

In another embodiment, a method for making the microfluidic assembly of FIGS. 1-3 are provided. FIG. 4A provides a perspective view of a mold 84 that can be used to form a device with a single triangular well while FIG. 4B provides a perspective view of a mold 86 that can be used to form device with a plurality (e.g., 4) triangular wells. The method includes a step of providing a mold (e.g., mold 84 or 86) having sidewalls that define a mold cavity 88. Characteristically, the mold cavity includes protrusion 90 for forming an input reservoir, protrusion 92 for forming at least one triangular well, protrusion 94 for forming an output reservoir; protrusion 96 for forming a first flow channel in fluid communication with the input reservoir and the at least one triangular well, and protrusion 98 for forming a second flow channel system in fluid communication with the output reservoir and the at least one triangular well. A curable resin is introduced into the mold cavity and then cured or allowed to cure. A polymeric block having the feature set forth above is removed from the mold cavity. The polymeric block is positioned between a first transparent plate and a second transparent plate. In a refinement, a gas-permeable membrane as set forth above is placed between the first transparent plate and a second transparent plate.

The following examples illustrate the various embodiments of the present invention. Those skilled in the art will recognize many variations that are within the spirit of the present invention and scope of the claims.

A variety of rapid prototyping and soft lithography techniques were used to fabricate a fluidic device that can house up to four adult zebrafish hearts in parallel with continuous media perfusion. To ensure compatibility with live imaging, the device confines each heart to a triangular chamber slightly larger than an average heart and the bottom of the device is an optically-clear acrylic panel. The device is also reversibly assembled so that hearts can be inserted and later removed for additional characterization, such as histology or gene or protein expression analysis. When cultured in the device, explanted adult zebrafish hearts experienced significantly fewer structural and functional declines compared to hearts cultured in Petri dishes over a one-week period. We also implemented our device to culture an injured adult zebrafish heart and successfully monitored regeneration using continuous live imaging over 4.5 days. Thus, our fluidic device enables unprecedented access to adult zebrafish heart regeneration, which can advance our fundamental knowledge of this process and potentially lead to the identification of molecules or processes that can translate to human heart repair.

Design and Fabrication of the Fluidic Device

Figure 5A:
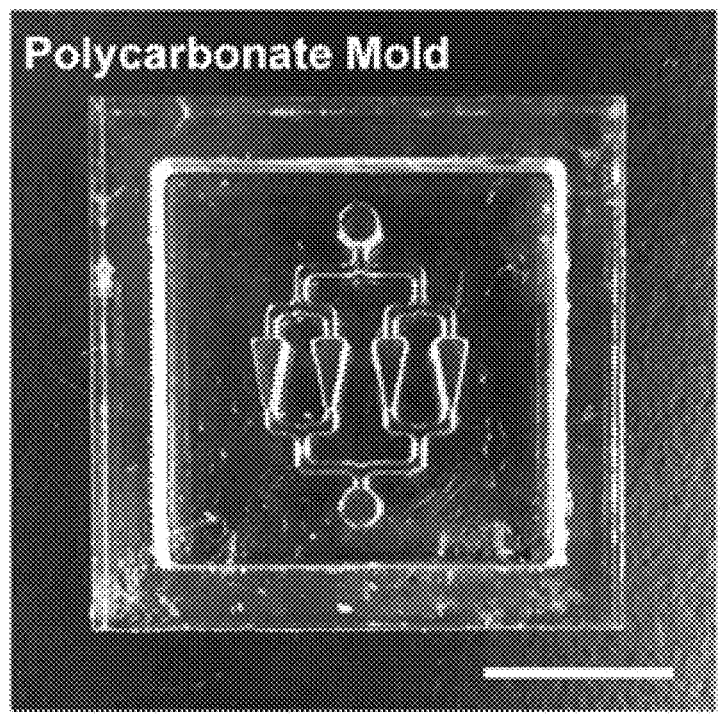
FIGS. 5A, 5B, and 5C. (A) Photograph of the micromilled polycarbonate template used to mold the PDMS slab. (B) Photograph of a complete assembled device. (C) Simulated fluid flow streamlines (red) and surface shear stresses (color bar) through a complete device (top) and a side view through a single well housing an average-sized heart (bottom). Scale bars are 10 mm for (A), and (B), and 1 mm for (C).

We designed a fluidic device (FIG. 1A) for culturing explanted adult zebrafish hearts that has the following components: (1) a PDMS slab embedded with a fluid path comprising inlet and outlet media reservoirs, a network of channels, and four triangular compartments that are slightly larger than an average adult zebrafish heart; (2) adaptors for connecting inlet and outlet reservoirs to tubing and a syringe pump for media perfusion; (3) a PTFE membrane for capturing and releasing air bubbles; (4) two transparent acrylic panels that compress the PDMS slab and PTFE membrane to enclose the fluid path; and (5) nuts and bolts for reversible device assembly. To fabricate the device, we milled the inverse of the fluid path into a piece of polycarbonate (FIG. 4B, FIG. 5A), which served as a master template for molding slabs of PDMS embedded with the fluid path. For each PDMS slab, we accessed the fluid path by punching inlet and output ports and inserting and sealing barbed nylon connectors that can interface with tubing. Next, we laser-cut the top and bottom panels from transparent 1.5 mm-thick acrylic sheets, which are thin enough to fit within the working distance of most low-numerical aperture or long working distance microscope objectives. We also laser-cut PTFE membranes and inserted one between each PDMS slab and top acrylic panel. Because PTFE is hydrophobic and gas-permeable, gas bubbles accumulate on PTFE and escape through the membrane under pressure (23). To vent the air bubbles collected by the PTFE membrane, we laser-cut rectangular voids into the top acrylic panel above the inlet and outlet channels. Because PTFE is opaque, we also laser-cut triangular holes in the PTFE membrane aligned above the triangular wells to avoid obstructing the imaging of the hearts.

Figure 5B:
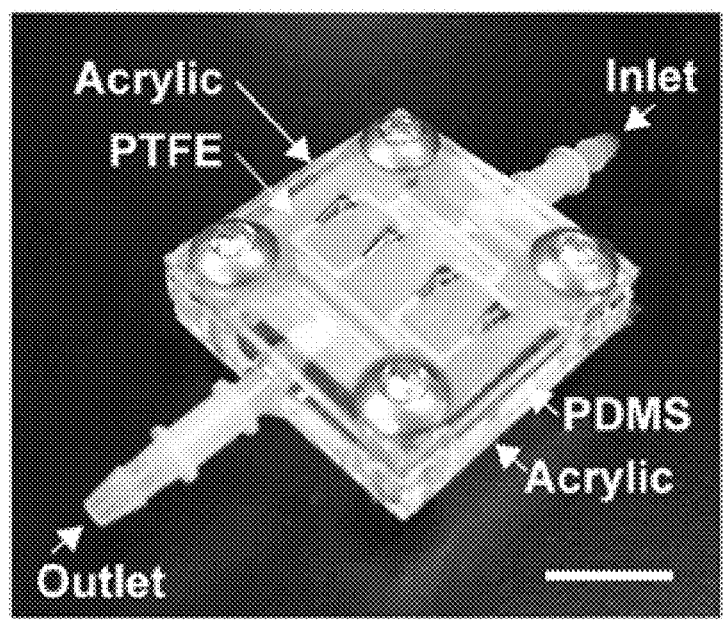

At the corners of the PDMS, PTFE membrane, and acrylic panels, we punched or laser-cut holes to accommodate bolts. When bolted between the two panels of acrylic and PTFE membrane, the elastomeric PDMS acts as a gasket and forms a liquid-tight seal around the wells and channels. However, because the components are not permanently bonded to each other, the device can be easily assembled and disassembled so that intact hearts can be placed in the device and then later retrieved for downstream analyses, such as histology or calcium imaging. The complete assembled device (FIG. 1B, FIG. 1C, FIG. 5B) has a footprint of 20 mm×20 mm to be compatible with most standard microscope stages.

Simulation of Flow and Shear Stresses in the Device

Figure 5C:
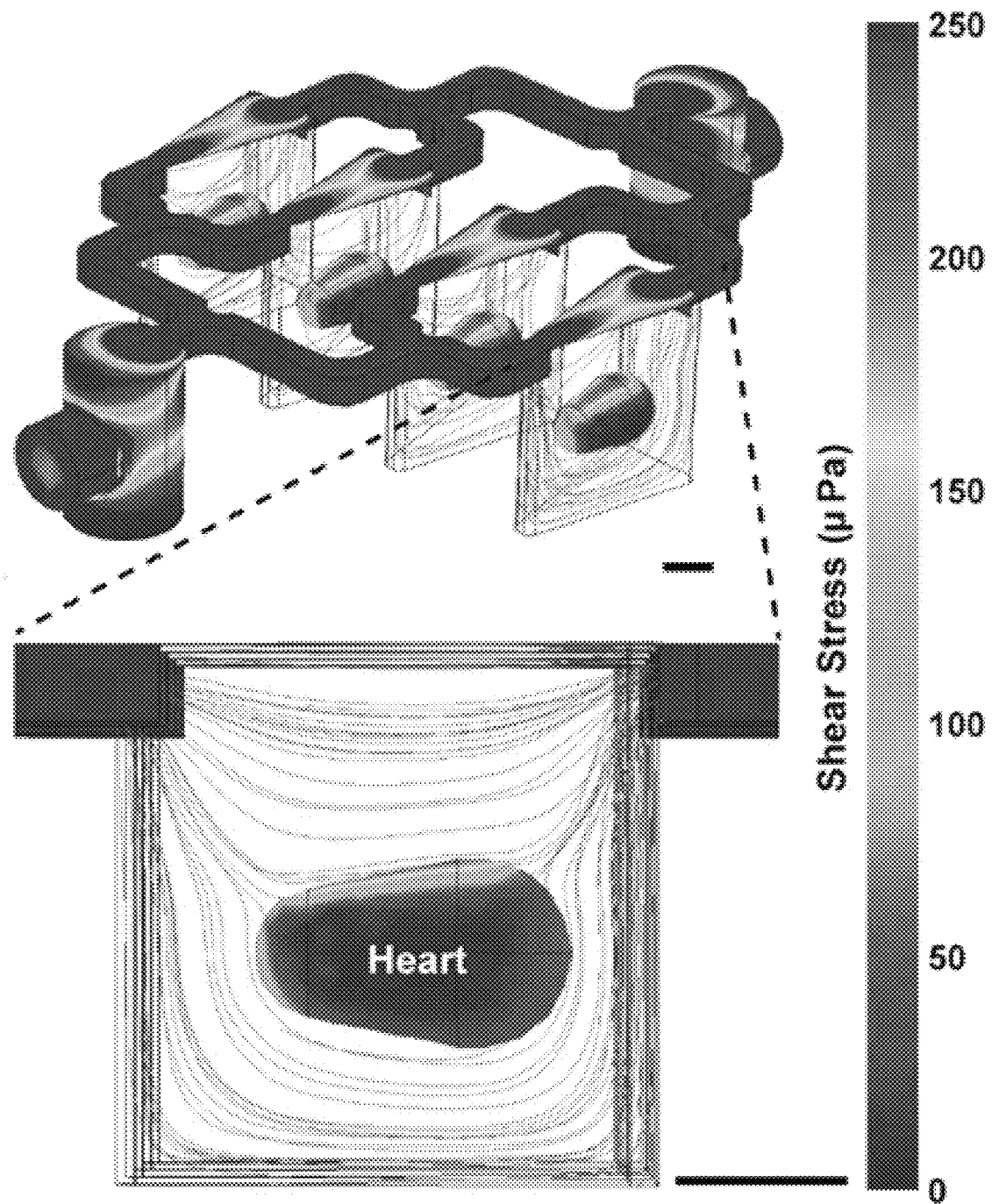

To perfuse media through our device, we chose a flow rate of 250 μL/hr because that is near the lower limit of most standard 60 mL syringe pumps and therefore was a practical choice for minimizing shear stress. To calculate shear stresses experienced by average zebrafish hearts cultured in the device at this flow rate, we used multi-physics modeling software. As shown by the fluid streamlines in FIG. 5C, our simulations predict that media is perfused throughout each compartment and that shear stresses reach a maximum of approximately 250 μPa on the top surface of the heart. This is well below the reported 1-3 Pa maximum shear stress applied to zebrafish heart walls during normal beating (24, 25), ensuring that hearts in the device do not experience supraphysiological shear stresses that may induce injury.

Because the total volume of the complete fluid path is approximately 78 μL, the media is completely refreshed approximately three times per hour. At this flow rate, the syringe pump can operate continuously for ten days without user intervention when using a full 60 mL syringe. This flow rate is also adequate for nutrient exchange because the standard practice for culturing explanted hearts is to exchange 3-5 mL of media every 1-2 days, which equates to approximately 60-200 μL/hr. Thus, a media perfusion rate of 250 μL/hr ensures that hearts have adequate media exchange without experiencing any injury from shear stress.

Structural Characterization of Cultured Hearts

Figure 6A:
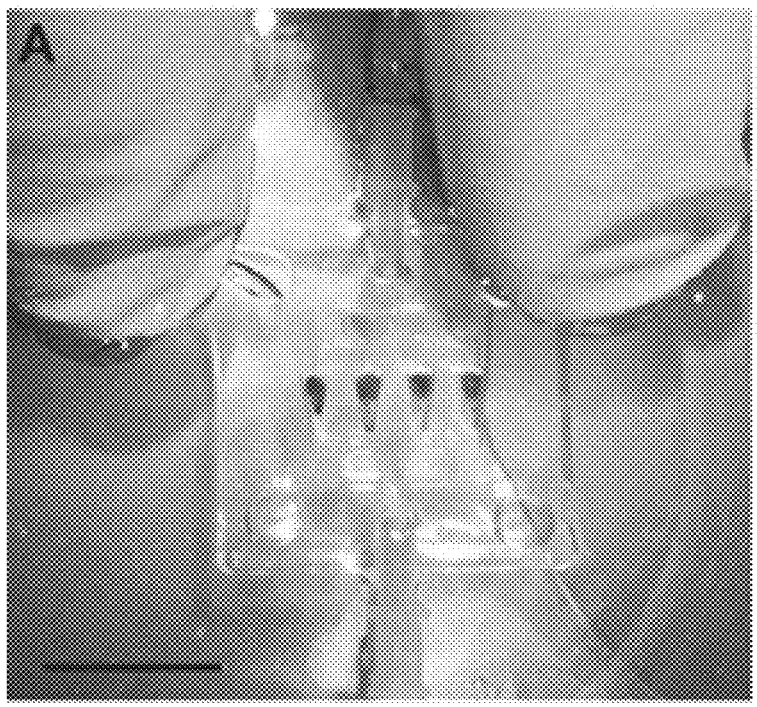
FIGS. 6A and 6B. Explanted zebrafish hearts in the fluidic device. (A) Photograph of PDMS slab immediately after loading with four explanted zebrafish hearts. Scale bar is 10 mm. (B) Fluorescent image of contracting heart explanted from fli1a:GFP transgenic zebrafish and imaged in the device. Image is a single frame from a movie of the hears. Scale bar is 200 μm.
Figure 6B:
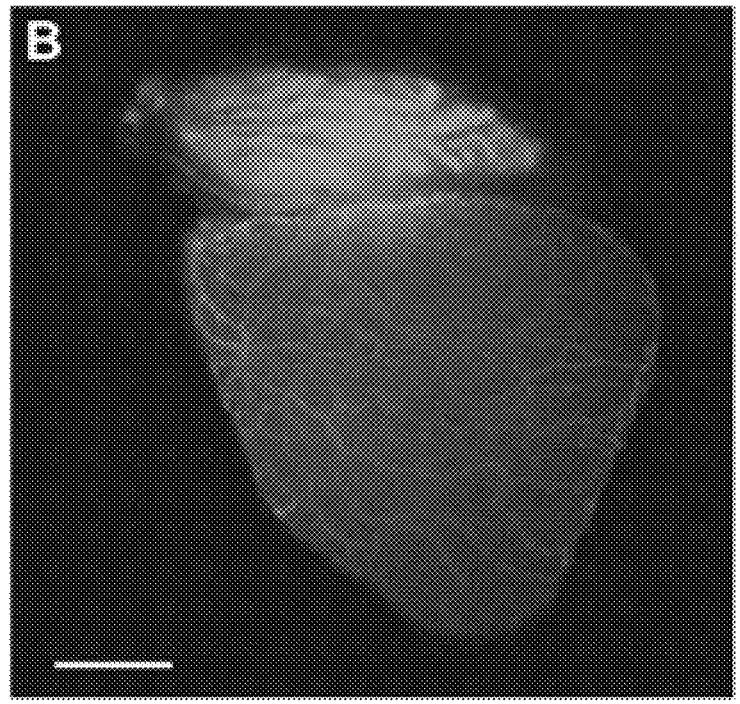

To evaluate the live imaging capabilities of our device, we next explanted hearts from adult transgenic zebrafish expressing the pan-endothelial marker fli1a:GFP (26) and placed them in a device to image the ventral aspect of the ventricle such that their outflow tracts were in-line with outlet channels (FIG. 6A). Because hearts retain some spontaneous beating, this orientation ensures that any heartgenerated flow through the lumen would be in alignment with pump-generated flow. We then connected the assembled device to a syringe pump, mounted the device on a fluorescent microscope, and initiated media perfusion. With a low-power objective, we could image through the bottom acrylic panel and record the GFP signal as the heart contracted (FIG. 6B). Because the heart was confined to a triangular compartment, its position stayed constant throughout the acquisition. This feature enables morphological features, such as changes in the geometry of the vascular network, to be easily tracked over multiple cardiac cycles.

Figure 7A:
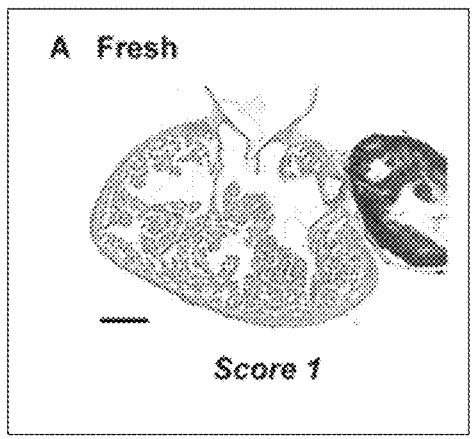
FIGS. 7A, 7B, 7C, 7D, 7E, 7F, and 7G. Structural characterization of Fresh and one- and two-week Dish and Device hearts. (A-E) AFOG-stained histology samples of hearts from the indicated experimental groups, with histology scores indicated. Scale bar is 200 μm. (F) Higher-resolution images of a sub-set of histology samples to illustrate increasing levels of abnormalities and corresponding scores. Scale bars is 50 μm. (G) Histology scores (1-3) for all hearts. *p<0.05 and **p<0.01 compared to Fresh hearts, according to the Kruskal-Wallis test followed by Dunn's multiple comparisons test to Fresh hearts. n=8, 8, 12, 8, and 9 for Fresh, one-week Dish, one-week Device, two-week Dish, and two-week Device hearts, respectively.
Figure 7B:
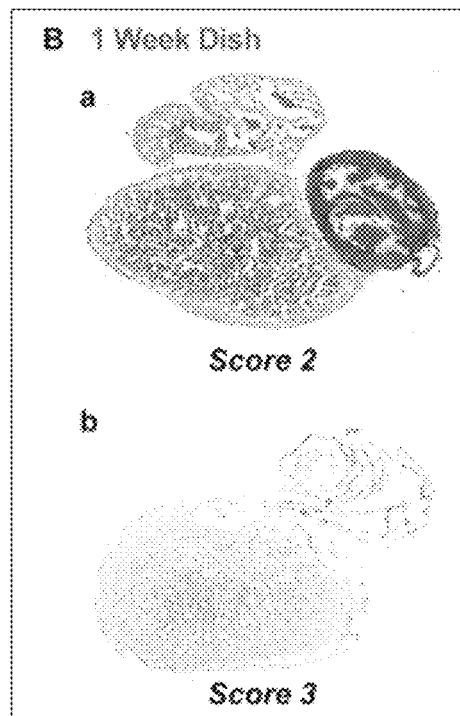
Figure 7C:
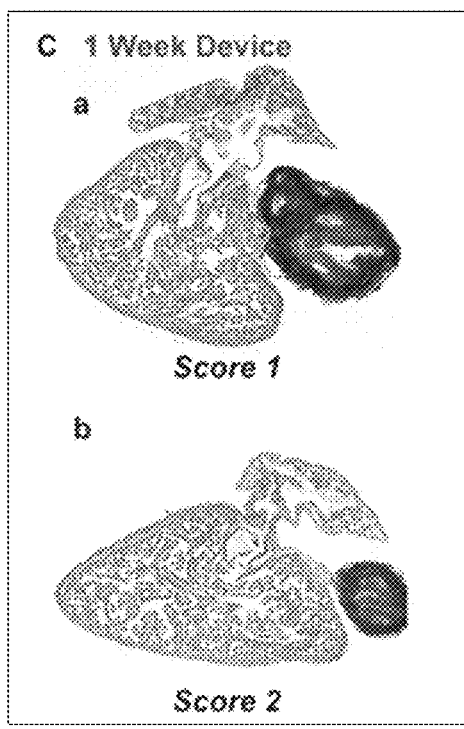
Figure 7D:
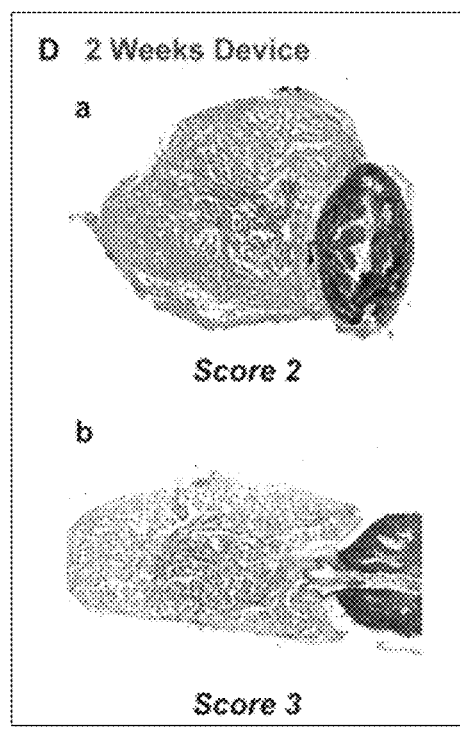
Figure 7E:
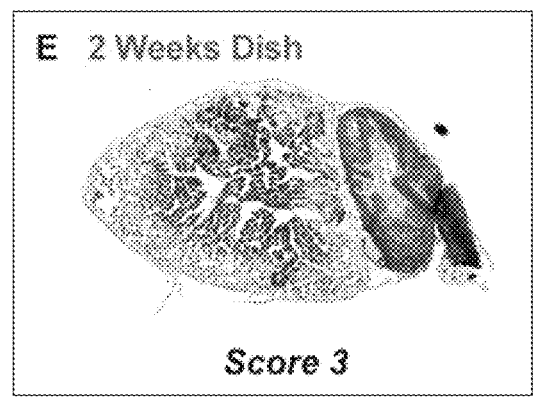

To determine if culturing hearts in the device extended their lifetime in culture, we next explanted hearts from adult wildtype zebrafish, loaded four hearts per device, connected each assembled device to a syringe pump, placed them in an incubator, and initiated media perfusion. At one- and two-week timepoints, we removed hearts from the device for histological staining. We also performed similar staining on freshly explanted hearts and hearts cultured in conventional Petri dishes for one and two week(s). In Fresh hearts, the myocardium was compact throughout the cortical and trabecular layers in all hearts (FIG. 7A), as expected. One-week Dish hearts showed varying amounts of structural degradation, including graining and discoloration of the myocardium (FIG. 7B). In most of these hearts, morphological changes were primarily localized to the cortical layer (FIG. 7Ba), but did extend into the trabecular layer in two of the eight hearts (FIG. 7Bb). In contrast, only two of the twelve one-week Device hearts showed abnormalities (FIG. 7C). Unlike the Dish hearts, these abnormalities appeared as a separation of the cortical and trabecular layers rather than a decrease in the integrity of the tissue itself, which still appeared relatively healthy (FIG. 7Cb). The remainder of the one-week Device hearts showed almost no signs of degradation and appeared similar to Fresh hearts (FIG. 7Ca). None of the one-week Device hearts showed any abnormalities in the inner trabecular layer of the myocardium. After two weeks, half of the Device hearts (FIG. 7D) and all Dish hearts (FIG. 7E) showed abnormal trabecular myocardium. Additionally, half of the Dish hearts presented with ectopic collagen staining within the myocardium.

Figure 7F:
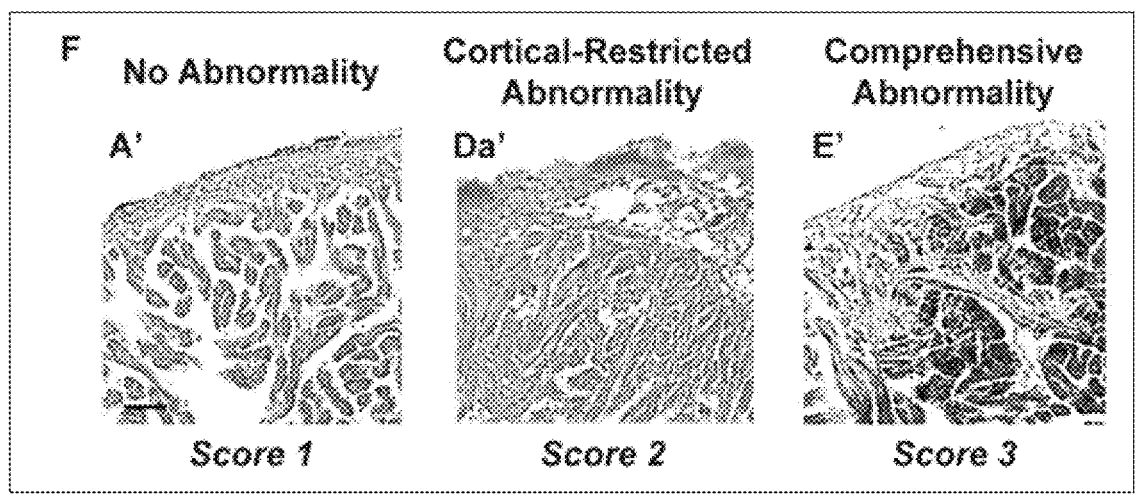
Figure 7G:
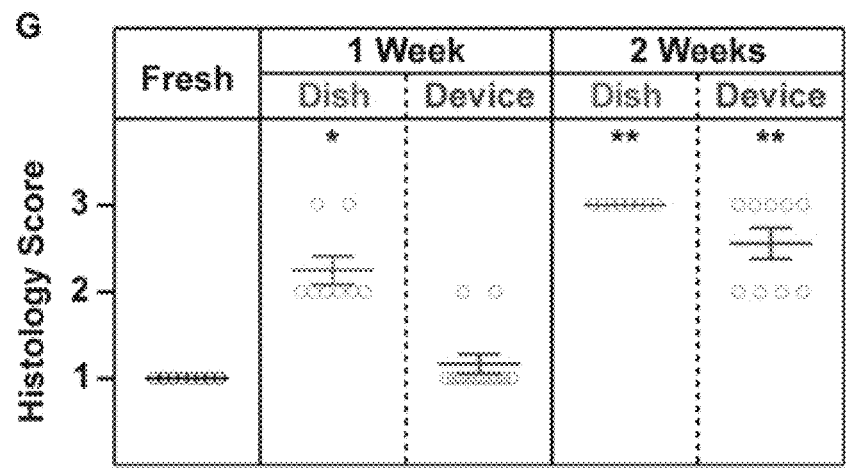

To quantify these observations, we scored the hearts from 1-3 based on the severity and positioning of any abnormal morphologies. The score was based on two descriptive categories: cortical abnormality or degradation (any abnormal morphology restricted to the outer layer of cardiac tissue), and extensive abnormality (any abnormal morphology or degradation that extends into the inner trabecular layer of cardiac tissue). Examples of abnormal morphologies and corresponding scores are shown in FIG. 7F. Combined histology scores (FIG. 7G) indicate that one-week Dish hearts had a significantly worse score than Fresh hearts ($p=0.0115$) whereas one-week Device hearts were not statistically different than Fresh hearts ($p>0.9999$). After two weeks, both Dish and Device hearts were significantly different than Fresh hearts ($p<0.0001$ and $p=0.0007$, respectively). These results suggest that culturing hearts in the fluidic device delayed degenerative processes observed in conventional culture conditions.

Functional Characterization of Cultured Hearts

Figure 8A:
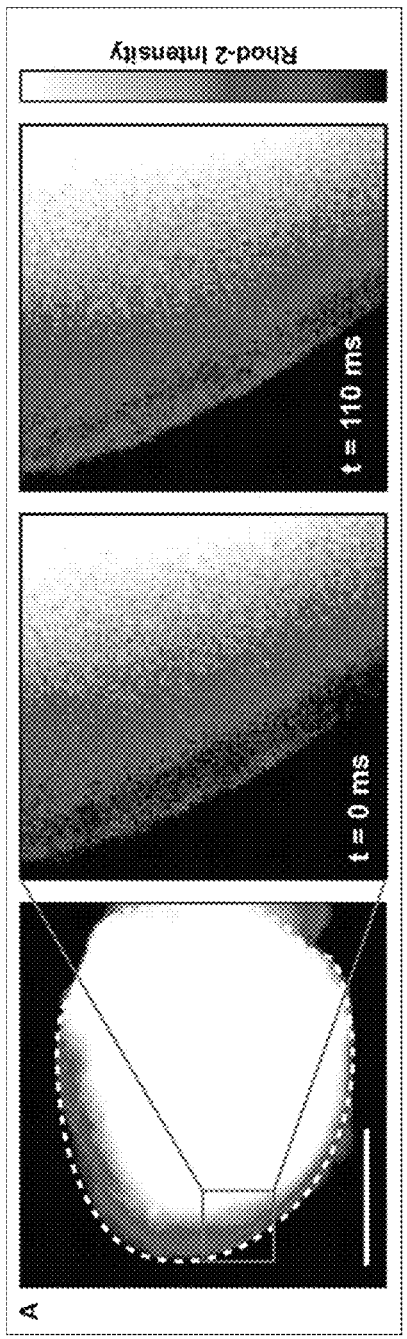
FIGS. 8A, 8B, 8C, 8D, and 8E. Imaging and analysis of calcium activity in Fresh and one- and two-week Dish and Device hearts. (A) Image of a one-week Device heart incubated with Rhod-2 and paced at 1 Hz. Higher resolution images illustrate changes in Rhod-2 intensity on the edges of the heart at rest (left image) and at the peak of the transient (right image). Scale bar is 500 μm. (B) Representative calcium transients from a Fresh heart (black), one-week Dish heart (blue), and one-week Device heart (red), each paced at 1.0 Hz. The circled time points correspond to the two smaller images in panel (A). (C) Capture rates for all hearts. *p<0.05 and **p<0.01 compared to Fresh hearts, according to the Kruskal-Wallis test followed by Dunn's multiple comparisons test to Fresh hearts. n=16, 10, 10, 11, and 12 for Fresh, one-week Dish, one-week Device, two-week Dish, and two-week Device hearts, respectively. (D) Rise and (E) decay times for all hearts. *p<0.05 and **p<0.01 compared to Fresh hearts, according to two-way ANOVA followed by Tukey's multiple comparisons test compared to Fresh hearts. n=10 for Fresh hearts at all frequencies; n=6 for one-week Dish hearts at all frequencies; n=9, 8, 7, and 8 for one-week Device hearts at 0.5, 1.0, 1.5, and 2.0 Hz, respectively.
Figure 8B:
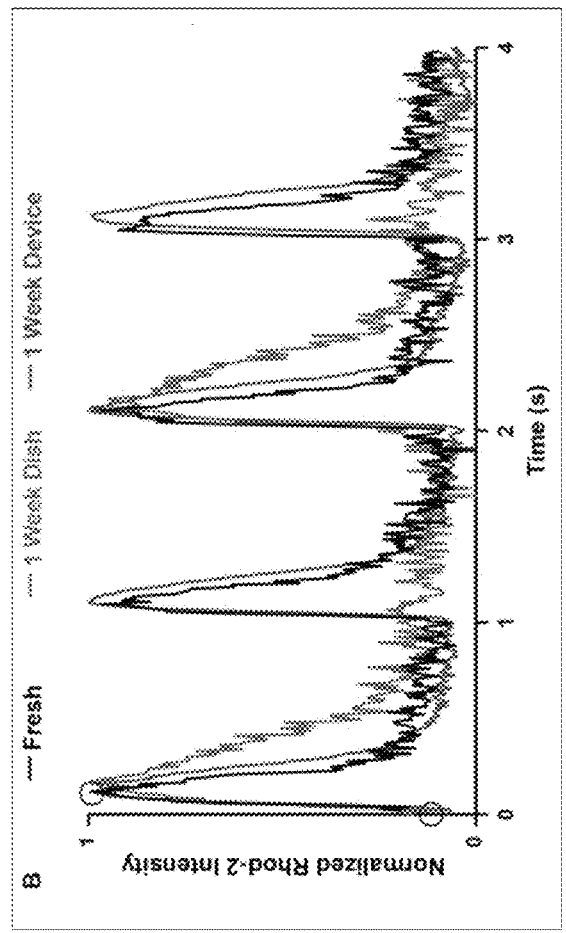
Figure 8C:
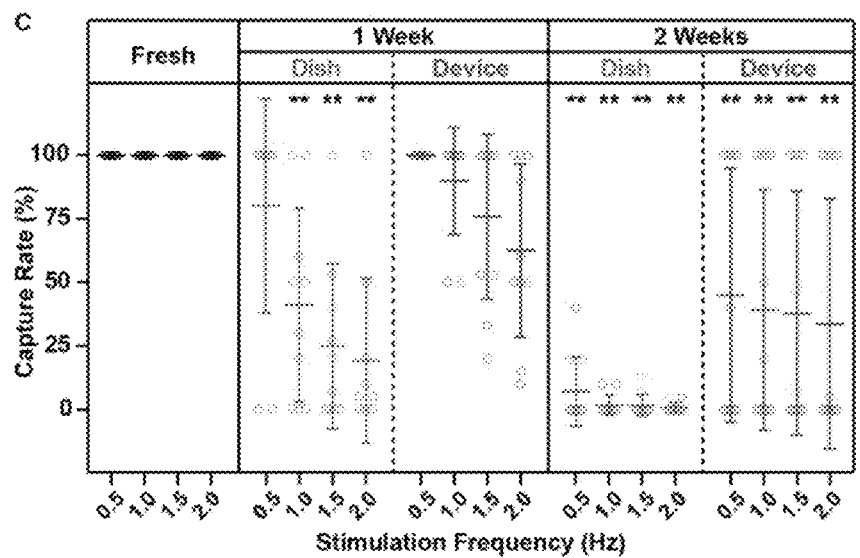

To characterize the functional properties of cultured hearts, we measured calcium activity in Fresh and one- and two-week Dish and Device hearts while pacing hearts at 0.5, 1.0, 1.5, and 2.0 Hz (FIG. 8A-B). First, we quantified the capture rate at each frequency (FIG. 8C), defined as the percentage of detectable calcium transients per stimulation pulse. As expected, Fresh hearts had a capture rate of 100±0% (n=9) at all four frequencies. One-week Dish hearts had capture rates of 80±42%, 41±38%, 25±33%, and 19±32% (n=10 for each) at 0.5, 1.0, 1.5, and 2.0 Hz, respectively. These values were significantly lower than Fresh hearts at 1.0, 1.5, and 2.0 Hz ($p=0.0047$, $p=0.0007$, and $p=0.0005$, respectively), indicative of pronounced physiological decline in Dish hearts. In contrast, one-week Device hearts had capture rates of 100±0%, 90±21%, 76±32%, and 63±34% (n=10 for each) at 0.5, 1.0, 1.5, and 2.0 Hz, respectively. These values were significantly similar to Fresh hearts at all frequencies ($p>0.9999$ at 0.5, 1.0, and 1.5 Hz and $p=0.3205$ at 2.0 Hz). These data suggest that Device hearts experienced fewer functional declines compared to Dish hearts after a one-week culture period.

Figure 8D:
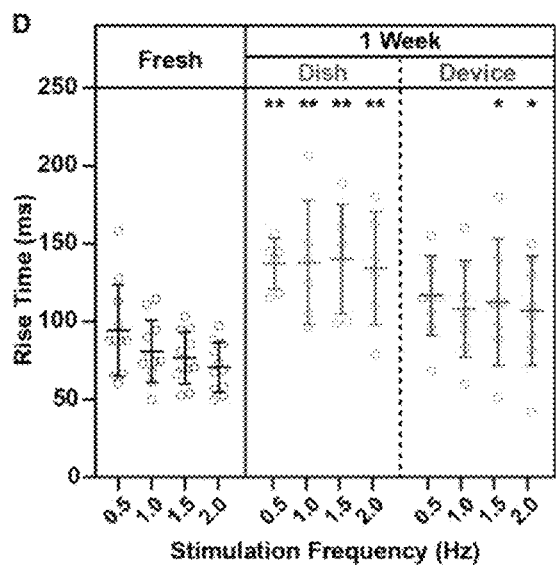
Figure 8E:
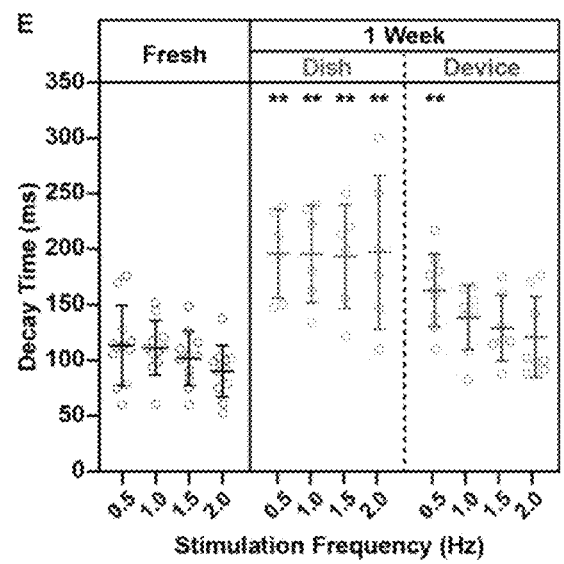

In addition to differences in capture rates, calcium transients from one-week Dish hearts appeared wider than Fresh hearts and one-week Device hearts (FIG. 8B). To quantify this, we calculated calcium transient rise (FIG. 8D) and decay (FIG. 8E) times. Because we can only analyze transients from hearts that responded to pacing, these comparisons are a subset of the data shown in FIG. 8C. At all stimulation frequencies, rise and decay times were significantly longer in Dish hearts compared to Fresh hearts ($p=0.0083$, $p=0.0003$, $p<0.0001$, and $p<0.0001$ for rise time at 0.5, 1.0, 1.5, and 2.0 Hz; $p<0.0001$ for decay times at 0.5, 1.0, 1.5, and 2.0 Hz). In contrast, the rise time for Device hearts was significantly longer than Fresh hearts only at 1.5 and 2.0 Hz ($p=0.1711$, $p=0.0858$, $p=0.0241$, and $p=0.0164$ at 0.5, 1.0, 1.5, and 2.0 Hz). Furthermore, the decay time for Device hearts was significantly longer than Fresh hearts only at 0.5 Hz ($p=0.0052$, $p=0.1866$, $p=0.2108$, and $p=0.1220$ at 0.5, 1.0, 1.5, and 2.0 Hz). Thus, in general, calcium transient dynamics in one-week Device hearts were more similar to Fresh hearts compared to one-week Dish hearts.

After two weeks of culture, most of the two-week Dish hearts were unresponsive to electrical stimulation, with average capture rates of 7±13%, 2±4%, 2±4%, and 1±2% at 0.5, 1.0, 1.5, 2.0 Hz, respectively (n=12 for each). In contrast, two-week Device hearts had capture rates of 45±50%, 39±47%, 38±48%, and 34±49% at these same frequencies (n=12 for each). Although two-week Device hearts were generally more responsive than two-week Dish hearts, the capture rates for both groups were significantly lower than Fresh hearts ($p<0.01$ for all comparisons), likely due in part to the wide variability in responses.

Live Imaging of Heart Regeneration Ex Vivo

Figure 9:
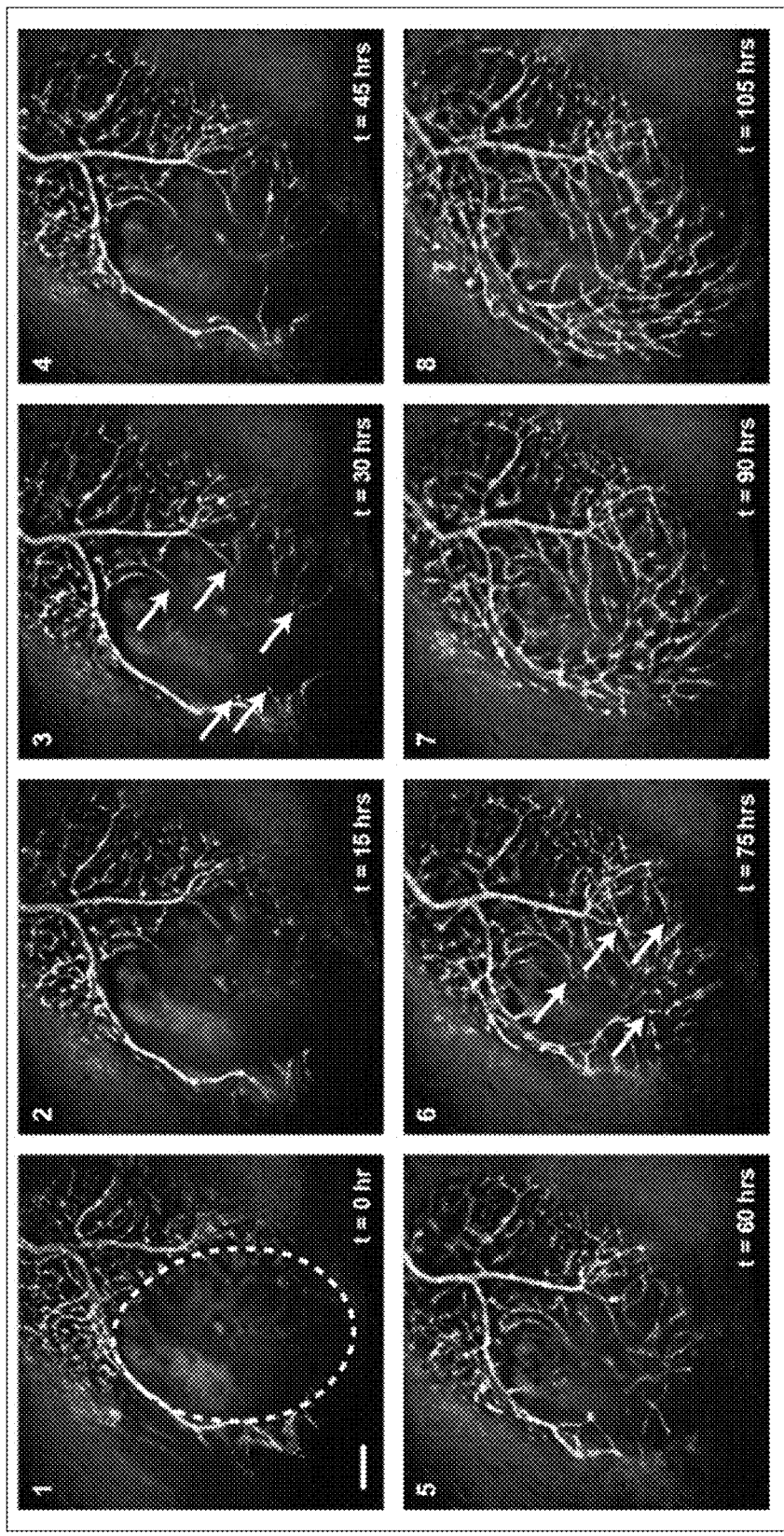
FIG. 9. Zebrafish heart regeneration ex vivo. A zebrafish heart underwent apex resection surgery followed by six days in vivo recovery. Live imaging of the apex wound site, demarcated with a dashed line (1), was then conducted on a six days post-amputation device-cultured adult transgenic zebrafish heart expressing the endothelial marker fli1a:GFP (magenta) and flt1enh:tdTomato (cyan). This time-lapse imaging shows migration of endothelial cells into the wound site (3) directly from the proximal vasculature. These cells form interconnections (6), followed by a visible restriction of the regenerated tissue around the wound site. Frames are selected from a movie of the hearts. Scale bar is 100 μm.

We next asked if adult zebrafish hearts maintain their regenerative capacity when cultured in the device and, if so, if we could visualize this process. To test this, we amputated zebrafish hearts expressing the pan-endothelial marker fli1a:GFP (26) and arterial specific marker flt1$^{enh}$:tdTomato (27) and allowed initial responses to the injury to proceed in vivo for six days. After the initial immune and wound healing responses subsided, we explanted the hearts, inserted them in the device such that the apex was at the base of the wells and bulbus arteriosus at the top so that we could observe regeneration of the vasculature, and collected an image every hour over the course of 4.5 days (FIG. 9). During this time, we observed the active migration of endothelial cells into the wound site from both coronary and non-arterial vessels proximal to the wound site between six and ten days post-amputation. It appears that most, if not all, vasculature was derived from this angiogenic migration from pre-existing proximal vasculature. We also observed that endothelial cells preceded, or migrated with, a progressive constriction around the wound site (FIG. 9-3). This may indicate that cells branching off the coronary vessels constrict the regenerating tissue around the wound site, which could be coupled to other regenerative processes. After projecting sprouts extended into the wound site, the endothelial cells formed interconnections with each other to generate the dense plexus (FIG. 9-6). Collectively, these data demonstrate that our device enables the visualization of regeneration in intact adult zebrafish hearts ex vivo, a process that has previously been inaccessible to live imaging.

Discussion

In distinct contrast to adult human hearts, adult zebrafish hearts are highly regenerative and can fully repair after severe injuries due to the orchestration of multiple cellular and extracellular components (5-14). Mechanisms driving zebrafish heart regeneration could potentially translate to therapeutics that restore the function of injured human hearts, but only after the details of this process are established. However, the in vitro (15-17) and ex vivo (18, 19) approaches that exist today provide limited insight into mechanisms of heart regeneration, especially the role of distinct cell types and their interactions after injury. To overcome these limitations, we fabricated a fluidic device for culturing explanted adult zebrafish hearts that continuously perfuses the hearts with media and immobilizes them to facilitate live imaging over several days. As shown by our histology and calcium transient data, our fluidic device extended the culture lifetime of explanted adult zebrafish hearts to one week in most cases and two weeks in some cases. Furthermore, we cultured an injured heart within our device and, over the course of 4.5 days, captured endothelial cells sprouting from existing vessels, migrating into a myocardial wound site, forming interconnections, and assembling a new vascular network that likely influences the migration and regeneration of other cell types. Previous lineage tracing data suggested that the likely source of this vasculature was existing endothelial cells, but could not distinguish between the existing coronary vasculature or the underlying endocardium (28). Confocal imaging of fixed cryoinjured hearts appeared to show actively migrating vasculature on the edge of the woundsite and suggested that revascularization is required for regeneration (12). Our observations confirm that this is the case, and further indicate that both arterial and non-arterial endothelial cells contribute to this regenerating population and appear to migrate in a coordinated fashion. Thus, our device enables unprecedented access to dynamic mechanisms of regeneration in intact adult zebrafish hearts, including cell migration, the origins of specialized tissues, and interactions between cardiac cell types. This approach can be widely adapted as a new experimental test-bed for establishing mechanisms of heart regeneration across molecular, cellular, and organ-level scales, especially because zebrafish are highly compatible with genomic modifications (29).

To design and fabricate our device, we used standard CAD software, microfabrication equipment, and low-cost materials. Thus, it is relatively straightforward to re-configure our device to accommodate other explanted organs or tissues of similar scale, including neonatal mouse hearts, which are also regenerative (30), or organoids, which can model a variety of developmental, physiological, and pathological processes (31, 32). These types of mm-scale, 3-dimensional tissue constructs could similarly benefit from the major features of our fluidic device: (1) intact tissues can be inserted and removed on-demand, (2) media is continuously perfused, and (3) live-imaging over long-term culture is feasible. Thus, our basic device framework has many applications for model systems beyond adult zebrafish hearts. However, one limitation of our device is that it is not compatible with high resolution imaging because the bottom panel is not glass, which is too brittle for our current design. We hope to address this problem in a future iteration of the device to enable dynamic imaging of processes on cellular and sub-cellular scales.

Intact zebrafish are currently being employed to screen the phenotypic effects of drugs because they have a rapid growth rate and are relatively easy and inexpensive to maintain, especially compared to rodents (33). For these same reasons, culturing explanted zebrafish hearts in our fluidic device could be implemented as a new tool for efficiently screening the safety and/or efficacy of drugs on the heart ex vivo. Although there are anatomical differences between zebrafish hearts and human hearts, they have many similarities in terms of their electrophysiology. For example, action potentials recorded from zebrafish cardiac myocytes have a relatively long duration and plateau phase (34, 35), which matches human cardiac myocytes more closely than mouse cardiac myocytes. This is especially advantageous for screening the arrhythmogenic effects of drugs (36). Additionally, due to their ease of genetic manipulation, mutations associated with arrhythmogenic diseases, such as Long QT Syndrome (37), can be easily introduced into zebrafish (38). Thus, hearts from transgenic zebrafish with human disease-relevant mutations could be explanted, cultured in our device, and used for live imaging and/or medium-throughput screening to efficiently identify potential therapeutic targets and molecules. Importantly, calcium transients recorded from hearts cultured in our fluidic device for one week were more similar to freshly isolated hearts compared to hearts cultured in conventional dishes. Thus, our device helped preserve some of the electrophysiological features of hearts in culture, improving their relevance for screening the arrhythmic or anti-arrhythmic effects of drugs. However, a limitation of our device is that it currently can only accommodate four hearts. Thus, our device would need to be modified to accommodate many more hearts to be useful for medium-throughput drug screening, which should be feasible with simple design modifications.

Materials and Methods

Experimental Design

The objective of this study was to fabricate a fluidic device for culturing explanted zebrafish hearts that extends their lifetime in culture and accommodates live imaging over several days. To evaluate the performance of our device, we implemented histology and calcium imaging techniques to quantify the structure and function, respectively, of hearts from the following experimental groups and endpoints: freshly explanted hearts ("Fresh hearts"), hearts cultured in the fluidic device for one or two weeks ("one-week Device hearts", "two-week Device hearts"), and hearts cultured in Petri dishes for one or two weeks ("one-week Dish hearts", "two-week Dish hearts"). Each experimental group consisted of 10-15 hearts, a sample size that is consistent with similar studies in this field. The study was not blinded and all data was included (i.e., outliers were not defined or excluded). For regeneration studies, hearts from previously characterized transgenic fish were used to visualize the revascularization of the wound area. We optimized the imaging parameters based on cellular toxicity and the speed of endothelial cell migration. This allowed us to live image the process of regeneration and observe the contribution of proximal vascular endothelial cells in 3 out of 4 replicates.

Fluidic Device Design and Fabrication

The fluid path (FIGS. 1-3) was designed using SolidWorks 2018 CAD Package (Dassault Systemes SolidWorks Corporation, Waltham, MA, USA) and consists of four parallel channels (0.5 mm×0.5 mm) that lead to a recessed triangular compartment (depth: 3.5 mm, length: 3.5 mm, base width: 1.75 mm). The four channels branch from a single inlet reservoir and merge into a single outlet reservoir with the same dimensions (radius: 2 mm, depth: 3 mm). For all channels and wells, sharp angles and intersections were rounded with fillets to minimize turbulence and air bubble accumulation. The fluid path was designed to fit within a 20 mm×20 mm slab.

The inverse of the fluid path and slab was milled from polycarbonate stock material using an Othermill V2 micromilling machine (Other Machine Co, Berkeley, CA, USA). All toolpaths were converted into g-code in Fusion360 (Autodesk, San Rafael, CA, USA) and run using Otherplan (Other Machine Co, Berkeley, CA, USA). The clearing strategy was based on a combination of adaptive roughing and horizontal and contour finishing using $\frac{1}{8}$", $\frac{1}{16}$", and $\frac{1}{32}$" flat end mills. The recommended tool settings based on polycarbonate clearing for spindle speed, cutting feed rate, plunge feed rate, and maximum stepdown size were taken from the manufacturer's website based on tool bit size. This polycarbonate template was vapor polished using previously described methods (39).

The polycarbonate template was used as a template for molding slabs of polydimethylsiloxane (PDMS, Sylgard 184; Dow Corning Corporation, Midland, MI, USA). PDMS was combined at a 10:1 (w/w) ratio of elastomer base to curing agent, mixed and degassed using a planetary centrifugal Thinky Mixer AR-100 (Thinky Corporation, Tokyo, Japan), poured into the polycarbonate template until it reached the top edge, and degassed again to remove residual air bubbles. The PDMS was cured at 65° C. for at least four hours and removed from the polycarbonate mold using tweezers. A 1.5 mm biopsy punch was used to create inlet and outlet channels leading to the inlet and outlet reservoirs in the PDMS slab. Barbed nylon connectors (inner diameter: $\frac{1}{16}$", McMaster-Carr, Elmhurst, IL, USA) were inserted into the inlet and outlet channels and sealed using PDMS to minimize leaking and provide more stability during device reuse.

The top and bottom acrylic panels of the device were designed using CorelDRAW X7 (Corel Corporation, Ottawa, Canada) software. To match the dimensions of the PDMS slab, 1.5 mm thick acrylic sheets (ePlastics, San Diego, CA, USA) were cut into 20 mm×20 mm squares using an Epilog Mini 18 (Epilog Laser, Golden, CO, USA) at 23% speed, 50% power, and 2500 Hz. Four holes with 3 mm diameter were cut in the panels equidistant from the corners to accommodate bolts. For the top acrylic panels, rectangular vents were cut above the inlet and outlet reservoirs to release gas bubbles collected by the polytetrafluoroethylene (PTFE) membrane, described below. The circular pieces from the holes and windows were removed using tweezers and the acrylic pieces were cleaned with sterile water to remove debris from the fabrication process. A 0.005" PTFE sheet (ePlastics, San Diego, CA, USA) was laser-cut at 12% speed, 10% power, and 2500 Hz into 20 mm×20 mm squares with voids located at the triangular compartments and bolt holes, matching the acrylic panels. PTFE membranes were brushed with uncured PDMS and bonded to the bottom surface of top acrylic panels for easier device assembly.

PDMS slabs were sandwiched between top and bottom acrylic panels and a 2.5 mm stainless steel biopsy punch was manually fed through the circular holes in the acrylic to create holes in the PDMS slab that were registered with the acrylic panels and PTFE membrane. At the time of experiments, a PDMS slab and PTFE membrane was clamped between a top and bottom acrylic panel using stainless steel, button head, Torx Plus bolts (thread size: 4-40, length: $\frac{3}{8}$", McMaster-Carr, Elmhurst, IL, USA) and narrow hex nuts (thread size: 4-40, height: $\frac{1}{16}$", McMaster-Carr, Elmhurst, IL, USA).

Multiphysics Modeling

Multiphysics modeling was performed using the finite element software package, COMSOL Multiphysics 5.3 (COMSOL Group, Stockholm, Sweden). The Reynolds number was calculated to be 0.0566 using the fluid velocity, density and viscosity of the media, and the dimensions of the channels. The scale of our device falls within the laminar flow regime; therefore, flow can be analyzed using the "laminar flow physics interface (spf)". The following assumptions were incorporated into the model: (i) the surface condition was set to no-slip because of the solid boundaries; (ii) the fluid was assumed to have the same density and viscosity as water; (iii) the inlet velocity was set to be a constant 0.25 mL/hr and the outlet surface was treated as a free surface, allowing fluid to pass through freely; (iv) the shear stress on the bounding surfaces was calculated by multiplying shear rate (COMSOL variable, spf.sr) with dynamic viscosity (user defined, spf.mu). Studies were conducted in stationary mode, as the conditions are steady-state. Velocity fields, streamlines, and surface shear stresses were plotted in various views and slices to show specific areas of interest, such as the center of the inlet and outlet channels and the surfaces of the hearts.

Zebrafish Heart Harvest and Culture for Fresh Hearts and Dish Hearts

Zebrafish lines Tg(fli1a:EGFP)$^{y1}$ (26) and Tg(-0.8flt1: RFP)$^{hu5333}$ (referred to as flt1$^{enh}$:tdtomato) (27) were raised and maintained at Children's Hospital Los Angeles (CHLA) under standard conditions of care and with CHLA Institutional Animal Care and Use Committee (IACUC) oversight. IACUC vetted and provided prior approval for all experimental procedures used in this study. Zebrafish were euthanized with Tricaine solution (4.2 mL of Tricaine stock in 100 mL of fish water) and positioned ventral side up in the groove of a moistened sponge under a dissecting microscope. The chest wall was opened with a longitudinal cut between the gills. The heart was gently pulled out of the chest cavity with a pair of tweezers holding the bulbus arteriosus and severed at the ventral aorta and sinus venosus using microscissors. The hearts were rinsed in Ringer's solution (115 mM sodium chloride, 2.9 mM potassium chloride, 1.8 mM calcium dichloride, 5 mM HEPES, pH 7.2 at 28° C.) three times before culturing. For Dish culture, 1 mL of pre-warmed media (DMEM, 10% FBS, 1:500 Primocin, 100 u$^{-1}$ Penicillin, 100 µg/mL Step, 2 µg/mL Heparin) was placed in a 12-well cell culture plate, into which one heart was placed per well and then statically incubated at 28.5° C. Media was replaced every second day using standard sterile culture techniques.

Loading Hearts Into Device

To culture hearts in the fluidic device, bolts were inserted through the four holes in a bottom acrylic panel and PDMS slab to hold these components together. The PDMS slab was pre-wet with 70% ethanol to minimize trapping of air bubbles and then submerged in Ringer's solution. Any air bubbles attached to the PDMS were dislodged by manual pipetting. Extracted zebrafish hearts were placed in each compartment with part of the ventricle fitting into the apex of the triangle. The top acrylic piece with the PTFE membrane was then positioned on top of the PDMS slab and secured by twisting a nut onto each bolt. Tubing was inserted onto the barbed connectors while the device was still submerged in Ringer's solution.

A programmable two-channel syringe pump (NE-4000, SyringePump.com, Suffolk, NY, USA) was used to perfuse media into the device through 1/16" ID, 1/8" OD PVC clear tubing (Masterkleer 5233K51, McMaster-Carr, Elmhurst, IL, USA). 60 mL syringes filled with pre-warmed maintenance media (DMEM, 10% FBS, 1:500 Primicin, 100 u$^{-1}$ Penicillin, 100 µg/mL Step, 2 µg/mL Heparin) were attached to tubing connected to the devices and loaded onto the syringe pump. All experiments were conducted at a perfusion rate of 0.25 mL/hr.

Histology and Structural Characterization

Hearts from each condition were fixed and processed for paraffin sectioning and Acid Fuchsin Orange G (AFOG) histology, as previously described (8). Sections were imaged using an optical microscope (Olympus BX51, Olympus Corporation, Tokyo, Japan). Images viewed using ImageJ were scored on the following criteria: normal morphology (similar to freshly isolated hearts) was considered Score 1, any morphology restricted to the outer (cortical) layer of cardiac tissue was considered Score 2, and any abnormal morphology in the inner (trabecular) layer or extending into this layer was considered Score 3.

Calcium Imaging and Analysis

Hearts from each condition were transferred to Petri dishes and incubated in 10 µM Rhod-2 AM (R1245MP, ThermoFisher Scientific, Waltham, MA, USA) in maintenance media for 20 minutes at 28° C. Samples were then rinsed and imaged in Tyrode's solution (0.5 mM HEPES, 0.1 mM magnesium chloride, 0.54 mM potassium chloride, 0.33 mM sodium phosphate, 1.8 mM calcium chloride, 5.0 mM glucose, pH 7.4 at 37° C.) with 15 µM blebbistatin to arrest contraction and minimize motion artifacts during data collection. Each Petri dish was moved to the stage of an inverted fluorescent microscope (Nikon Eclipse Ti, Nikon Corporation, Tokyo, Japan) enclosed in a 28° C. incubation chamber (OKOLAB USA Inc., San Bruno, CA, USA). A platinum point electrode was connected to a stimulator (MyoPacer MYP100, IonOptix, Westwood, MA, USA) and positioned into the dish approximately 2-3 mm away from the hearts using a micro-manipulator (Patchman NP 2, Eppendorf, Hauppauge, NY, USA). The electrode was used to deliver 35 V biphasic, charge-balanced pulses at 0.5, 1.0, 1.5, and 2.0 Hz. Fluorescence of the calcium transients was captured using a 10× air objective and a high-speed camera (Andor Zyla sCMOS, Oxford Instruments, Abingdon, UK) at 100 frames per second, 4×4 binning, and a gain of 4.

Calcium transients were extracted by plotting average fluorescent intensity of a 100×100 pixel region of interest using ImageJ. These values were then processed using custom MATLAB software (MATLAB, MathWorks, Natick, MA, USA), similar to previous studies (40). After calculating the period of the transients within each trace with a Fourier transform, a peak detection algorithm was used to automatically split each trace into individual transients. Each transient was analyzed to calculate rise time and decay times. The largest sustained fluorescence increase was identified as the rising slope of the transient. Backtracking in time until the slope changed from positive to negative provided the start time and background fluorescence signal. The rise time was found by subtracting this start time from the time of the maximum intensity. To find the decay time, the background brightness value was subtracted from the maximum brightness to find a normalized maximum brightness. Then, the time until this normalized brightness signal fell by 50% was calculated and defined as the decay time.

Live Imaging

Hearts were resected as previously described (8) and then isolated into Ringer's solution containing 100 µg/mL Primocin and 150 U/mL heparin from terminally anesthetized transgenic zebrafish after six days post-amputation. Isolated hearts were then transferred to wells of a device and hooked up to the media perfusion system. The device was perfused with media within the live imaging chamber of a fluorescent microscope (Leica DM IRE2, Leica Microsystems, Wetzlar, Germany) over four to six days. Four hearts (in separate wells) were perfused in L-15 media supplemented with 10% FCS, 100 µg/mL Primocin, 1.25 mM $CaCl_2$, and 800 mg/L glucose at a rate of 0.3 mL/hr. µManager acquisition software (41) was used to capture a predefined z stack of images every hour for the duration of the experiment. Acquired images were then concatenated and cropped in ImageJ, and deconvolved using AutoQuant X3 (Media Cybernetics Inc, Rockville, MD). Finally, focus and brightness fluctuation were corrected using Gaussian Focus and Brightness Normalizer plug-ins (supplemental downloads) in ImageJ.

Statistical Analysis

Statistical analysis was performed using GraphPad Prism 8 (GraphPad Software Inc., San Diego, CA, USA). All data are plotted as individual data points (biological replicates), with lines indicating the mean and error bars representing the standard deviation of the mean. A p value of less than 0.05 was considered statistically significant. All datasets were first tested for normality using the Shapiro-Wilk test. For histology scoring and capture rate measurements, data was not normally distributed and thus the Kruskal-Wallis test followed by Dunn's multiple comparisons test was used to compare the control group (Fresh) to each experimental group (one- and two-week Dish and Device hearts). For calcium transient rise and decay times, data was normally distributed and thus two-way ANOVA followed by Tukey's multiple comparisons test was used to compare the control group to each experimental group. For capture rate and calcium transient rise and decay times, each frequency (0.5, 1.0. 1.5, and 2.0 Hz) was statistically compared independently.

While exemplary embodiments are described above, it is not intended that these embodiments describe all possible forms of the invention. Rather, the words used in the specification are words of description rather than limitation, and it is understood that various changes may be made without departing from the spirit and scope of the invention. Additionally, the features of various implementing embodiments may be combined to form further embodiments of the invention.

REFERENCES

1. M. A. Laflamme, C. E. Murry, Heart regeneration. *Nature* 473, 326-335 (2011).
2. P. Staat, G. Rioufol, C. Piot, Y. Cottin, T. T. Cung, I. L'Huillier, J. F. Aupetit, E. Bonnefoy, G. Finet, X. André-Fouët, M. Ovize, Postconditioning the human heart. *Circulation* 112, 2143-2148 (2005).
3. J. O. Oberpriller, J. C. Oberpriller, Response of the adult newt ventricle to injury. *J Exp Zool* 187, 249-253 (1974).
4. T. Borchardt, T. Braun, Cardiovascular regeneration in non-mammalian model systems: what are the differences between newts and man? *Thromb Haemost* 98, 311-318 (2007).
5. J. Bloomekatz, M. Galvez-Santisteban, N. C. Chi, Myocardial plasticity: cardiac development, regeneration and disease. *Curr Opin Genet Dev* 40, 120-130 (2016).
6. J. M. Gonzalez-Rosa, C. E. Burns, C. G. Burns, Zebrafish heart regeneration: 15 years of discoveries. *Regeneration (Oxf)* 4, 105-123 (2017).
7. N. Rubin, M. R. Harrison, M. Krainock, R. Kim, C. L. Lien, Recent advancements in understanding endogenous heart regeneration-insights from adult zebrafish and neonatal mice. *Semin Cell Dev Biol* 58, 34-40 (2016).
8. K. D. Poss, L. G. Wilson, M. T. Keating, Heart regeneration in zebrafish. *Science* 298, 2188-2190 (2002).
9. K. Kikuchi, J. E. Holdway, A. A. Werdich, R. M. Anderson, Y. Fang, G. F. Egnaczyk, T. Evans, C. A. Macrae, D. Y. Stainier, K. D. Poss, Primary contribution to zebrafish heart regeneration by gata4(+) cardiomyocytes. *Nature* 464, 601-605 (2010).
10. C. Jopling, E. Sleep, M. Raya, M. Marti, A. Raya, J. C. Izpisua Belmonte, Zebrafish heart regeneration occurs by cardiomyocyte dedifferentiation and proliferation. *Nature* 464, 606-609 (2010).
11. A. Lepilina, A. N. Coon, K. Kikuchi, J. E. Holdway, R. W. Roberts, C. G. Burns, K. D. Poss, A dynamic epicardial injury response supports progenitor cell activity during zebrafish heart regeneration. *Cell* 127, 607-619 (2006).
12. R. Marin-Juez, M. Marass, S. Gauvrit, A. Rossi, S. L. Lai, S. C. Materna, B. L. Black, D. Y. Stainier, Fast revascularization of the injured area is essential to support zebrafish heart regeneration. *Proc Natl Acad Sci USA* 113, 11237-11242 (2016).
13. M. Harrison, X. Feng, Q. Mo, A. Aguayo, J. Villafuerte, T. Yoshida, C. Pearson, S. Schulte-Merker, C. Lien, Late developing cardiac lymphatic vasculature supports adult zebrafish heart function and regeneration. *eLife*.
14. W. C. Chen, Z. Wang, M. A. Missinato, D. W. Park, D. W. Long, H. J. Liu, X. Zeng, N. A. Yates, K. Kim, Y. Wang, Decellularized zebrafish cardiac extracellular matrix induces mammalian heart regeneration. *Sci Adv* 2, e1600844 (2016).
15. J. Kim, N. Rubin, Y. Huang, T. L. Tuan, C. L. Lien, In vitro culture of epicardial cells from adult zebrafish heart on a fibrin matrix. *Nat Protoc* 7, 247-255 (2012).
16. V. Sander, G. Surae, C. Jopling, C. Morera, J. C. Izpisua Belmonte, Isolation and in vitro culture of primary cardiomyocytes from adult zebrafish hearts. *Nat Protoc* 8, 800-809 (2013).
17. C. L. Lien, M. Schebesta, S. Makino, G. J. Weber, M. T. Keating, Gene expression analysis of zebrafish heart regeneration. *PLoS biology* 4, e260 (2006).
18. S. Pieperhoff, K. S. Wilson, J. Baily, K. de Mora, S. Maqsood, S. Vass, J. Taylor, J. Del-Pozo, C. A. MacRae, J. J. Mullins, M. A. Denvir, Heart on a plate: histological and functional assessment of isolated adult zebrafish hearts maintained in culture. *PloS one* 9, e96771 (2014).
19. J. Cao, K. D. Poss, Explant culture of adult zebrafish hearts for epicardial regeneration studies. *Nat Protoc* 11, 872-881 (2016).
20. J. Akagi, K. Khoshmanesh, B. Evans, C. J. Hall, K. E. Crosier, J. M. Cooper, P. S. Crosier, D. Wlodkowic, Miniaturized embryo array for automated trapping, immobilization and microperfusion of zebrafish embryos. *PLoS One* 7, e36630 (2012).
21. L. L. Bischel, B. R. Mader, J. M. Green, A. Huttenlocher, D. J. Beebe, Zebrafish Entrapment By Restriction Array (ZEBRA) device: a low-cost, agarose-free zebrafish mounting technique for automated imaging. *Lab Chip* 13, 1732-1736 (2013).
22. M. Erickstad, L. A. Hale, S. H. Chalasani, A. Groisman, A microfluidic system for studying the behavior of zebrafish larvae under acute hypoxia. *Lab Chip* 15, 857-866 (2015).
23. C. Liu, J. A. Thompson, H. H. Bau, A membrane-based, high-efficiency, microfluidic debubbler. *Lab Chip* 11, 1688-1693 (2011).
24. V. Vedula, J. Lee, H. Xu, C. J. Kuo, T. K. Hsiai, A. L. Marsden, A method to quantify mechanobiologic forces during zebrafish cardiac development using 4-D light sheet imaging and computational modeling. *PLoS Comput Biol* 13, e1005828 (2017).
25. F. Boselli, J. Vermot, Live imaging and modeling for shear stress quantification in the embryonic zebrafish heart. *Methods* 94, 129-134 (2016).
26. N. D. Lawson, B. M. Weinstein, In vivo imaging of embryonic vascular development using transgenic zebrafish. *Developmental biology* 248, 307-318 (2002).
27. J. Bussmann, F. L. Bos, A. Urasaki, K. Kawakami, H. J. Duckers, S. Schulte-Merker, Arteries provide essential guidance cues for lymphatic endothelial cells in the zebrafish trunk. *Development* 137, 2653-2657 (2010).
28. L. Zhao, A. L. Borikova, R. Ben-Yair, B. Guner-Ataman, C. A. MacRae, R. T. Lee, C. G. Burns, C. E. Burns, Notch signaling regulates cardiomyocyte proliferation during zebrafish heart regeneration. *Proc Natl Acad Sci USA* 111, 1403-1408 (2014).
29. E. Lin, S. Shafaattalab, J. Gill, B. Al-Zeer, C. Craig, M. Lamothe, K. Rayani, M. Gunawan, A. Y. Li, L. Hove-Madsen, G. F. Tibbits, Physiological phenotyping of the adult zebrafish heart. *Mar Genomics*, 100701 (2019).
30. E. R. Porrello, A. I. Mahmoud, E. Simpson, J. A. Hill, J. A. Richardson, E. N. Olson, H. A. Sadek, Transient regenerative potential of the neonatal mouse heart. *Science* 331, 1078-1080 (2011).
31. M. A. Lancaster, J. A. Knoblich, Organogenesis in a dish: modeling development and disease using organoid technologies. *Science* 345, 1247125 (2014).
32. D. Dutta, I. Heo, H. Clevers, Disease Modeling in Stem Cell-Derived 3D Organoid Systems. *Trends Mol Med* 23, 393-410 (2017).

33. C. A. MacRae, R. T. Peterson, Zebrafish as tools for drug discovery. *Nature reviews. Drug discovery* 14, 721-731 (2015).
34. C. A. Macrae, Cardiac Arrhythmia: In vivo screening in the zebrafish to overcome complexity in drug discovery. *Expert Opin Drug Discov* 5, 619-632 (2010).
35. M. Vornanen, M. Hassinen, Zebrafish heart as a model for human cardiac electrophysiology. *Channels (Austin)* 10, 101-110 (2016).
36. D. J. Milan, I. L. Jones, P. T. Ellinor, C. A. MacRae, In vivo recording of adult zebrafish electrocardiogram and assessment of drug-induced QT prolongation. *Am J Physiol Heart Circ Physiol* 291, H269-273 (2006).
37. R. Arnaout, T. Ferrer, J. Huisken, K. Spitzer, D. Y. Stainier, M. Tristani-Firouzi, N. C. Chi, Zebrafish model for human long QT syndrome. *Proceedings of the National Academy of Sciences of the United States of America* 104, 11316-11321 (2007).
38. A. Pott, W. Rottbauer, S. Just, Functional genomics in zebrafish as a tool to identify novel antiarrhythmic targets. *Current medicinal chemistry* 21, 1320-1329 (2014).
39. D. P. Yen, Y. Ando, K. Shen, A cost-effective micromilling platform for rapid prototyping of microdevices. *Technology (Singap World Sci)* 4, 234-239 (2016).
40. A. P. Petersen, D. M. Lyra-Leite, N. R. Ariyasinghe, N. Cho, C. M. Goodwin, J. Y. Kim, M. L. McCain, Microenvironmental Modulation of Calcium Wave Propagation Velocity in Engineered Cardiac Tissues. *Cellular and molecular bioengineering*, (2018).
41. A. Edelstein, N. Amodaj, K. Hoover, R. Vale, N. Stuurman, Computer control of microscopes using μManager. *Curr Protoc Mol Biol* Chapter 14, Unit 14.20 (2010).

What is claimed is:

1. A method for imaging an explanted organ in a microfluidic assembly, the microfluidic assembly comprising:
   a polymeric block having a top surface and a bottom surface, the polymeric block defining:
     an input reservoir;
     at least one triangular well;
     an output reservoir;
     a first flow channel system in fluid communication with the input reservoir and the at least one triangular well;
     a second flow channel system in fluid communication with the output reservoir and the at least one triangular well, wherein the first flow channel system and the second flow channel system each independently include tracks having a closed bottom and open top;
     an inlet conduit in fluid communication with the input reservoir;
     an outlet conduit in fluid communication with the output reservoir;
   a first transparent plate disposed over the top surface of the polymeric block; and
   a second transparent plate disposed over the bottom surface of the polymeric block, the method comprising:
     placing an explanted organ into the at least one triangular well;
     continuingly flowing a culture medium into the microfluidic assembly; and
     imaging the explanted organ.

2. The method of claim 1 wherein the microfluidic assembly includes a plurality of triangular wells with an explanted organ or organoid being placed into each triangular well.

3. The method of claim 1 wherein the explanted organ is a zebrafish heart.

4. The method of claim 1 wherein the culture medium includes a fluorescent dye, indicator, or toxic/therapeutic agent.

* * * * *